(12) United States Patent
Morgan

(10) Patent No.: US 6,759,201 B2
(45) Date of Patent: Jul. 6, 2004

(54) METHOD OF IDENTIFYING A NEURAL PROGENITOR CELL BY EVALUATING EXPRESSION OF DAEDALOS

(75) Inventor: Bruce A. Morgan, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/037,667

(22) Filed: Oct. 25, 2001

(65) Prior Publication Data

US 2002/0177145 A1 Nov. 28, 2002

Related U.S. Application Data

(60) Provisional application No. 60/243,110, filed on Oct. 25, 2000.

(51) Int. Cl.[7] .............................. C12Q 1/68; C12Q 1/02; G01N 33/53
(52) U.S. Cl. ............................... 435/6; 435/7.1; 435/29
(58) Field of Search ................................ 435/6, 7.1, 29

(56) References Cited

PUBLICATIONS

Chiasson et al., "Adult Mammalian Forebrain Ependymal and Subependymal . . . ", (1999) J. Neuroscience 19(11):4462–4471.
Corotto et al., "Neurogenesis persists in the subependymal layer of adult mouse brain", (1993) Neurosci Letter 149:111–114.
Georgopoulos et al., "The Role of The Ikaros Gene . . . ", (1997) Annu. Rev. Immunol. 15:155–176.
Greene et al., "Establishment of a noradrenergic clonal line . . . ", (1976) Proc. Natl. Acad. Sci. USA 73:2424–2428.
Honma et al., "Eos: a novel member of the Ikaros gene family . . . ", (1999) FEBS Letters 447:76–80.
Johansson et al., "Identification of a Neural Stem in the Adult . . . ", (1999) Cell 96(1):25–34.
Kelley et al.. "Helios, a novel dimerization partner of Ikaros . . . ", (1998) Curr. Biol, 8(9):508–515.
Kim et al., "Ikaros DNA–Binding Proteins Direct Formation . . . ", (1999) Immunity 10(3):345–355.
Luskin et al., "Restricted Proliferation and Migration of Postnatally . . . ", (1993) Neuron 11(1):173–189.
Morgan et al., "Aiolos a lymphoid restricted transcription factor that interacts . . . ", (1997) EMBO J 16(8):2004–2013.
Palmer et al., "The Adult Rat Hippocampus Contains . . . ", (1997) Mol. Cell. Neurosci. 8(6):389–404.
Sun et al., "Zinc finger–mediated protein interactions modulate Ikaros activity, . . . ", (1996) EMBO J 15(19):5358–5369.
Sally Temple, "CNS developement: The obscure origins of adult stem cells", (1999) Curr. Biol. 9(11):R397–R399.
Wang et al., "Aiolos Regulates B Cell Activation . . . ", (1998) Immunity 9(4):543–553.
Kiyosawa et al., "Expression of analysis of the novel transcription factor . . . ", 1999, Society for Neuroscience Abstracts, vol. 25(1–2);252.
Dobi et al., "Sample and probe: a novel approach for identifying . . . ", 1997, Molecular Brain Research, vol. 52(1);98–111.
International Search Report for PCT/US01/51164; mailed Mar. 13, 2003.

*Primary Examiner*—Terry McKelvey
(74) *Attorney, Agent, or Firm*—Fish & Richardson P.C.

(57) ABSTRACT

The invention provides Daedalos polypeptides, nucleic acids encoding Daedalos polypeptides, and methods of using Daedalos polypeptides and nucleic acids. Also included in the invention are methods of diagnosis, methods of treatment, methods of detection, and methods of controlling neural cell differentiation by detecting and/or modulating expression of Daedalos in a cell.

9 Claims, 4 Drawing Sheets

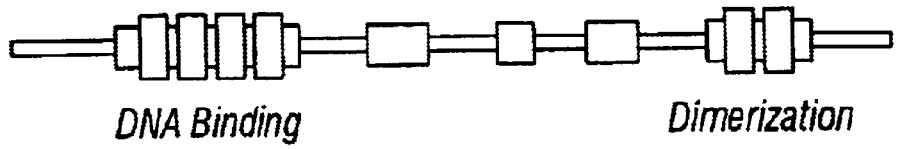

DNA Binding          Dimerization

FIG. 1A

```
         1                                                    50
DAED  ---------- ---MESLFCE SSGDSSLEKE FLGAPVGPSV STPNSQHSSP
HEL   ---MHCTLTM ETDAIDGYIT CDNELSPEGE HANMAIDLTS STPNGQQASP
AIO   -MEDIQPTVE LKSTEEQPLP TESPDALNDY SLPKPHEIEN VDSREAPANE
IK    MDVDEGQDMS QVSGKESPPV SDTPDE.GDE PMPVPEDLST TSGAQQNSKS
         51                                                   100
DAED  SRSLSANSIK VEMYSDEESS RL.LGPDERL LDKDDSVIVE DSLSEPLGYC
HEL   SHMTSTNSVK LEMQSDEECD RQPLSREDEI RGHDEGSSLE EALIESSEVA
AIO   DEDAGEDSMK VKDEYSDRDE N..IMKPEPM GDAEESEM.P YSYAREYSDY
IK    DRGMA.SNVK VETQSDEENG R..ACEMNGE ECAEDLRMLD ASGEKMNGSH
         101                                                  150
DAED  DGSGPEP.HS PGGIRLPNGK LKCDVCGMVC IGPNVLMVHK RSHTGERPFH
HEL   DNRKVQDLQG ERGIRLPNGK LKCDVCGMVC IGPNVLMVHK RSHTGERPFH
AIO   ESIKLERHVP YDNSRPTSGK MNCDVCGLSC ISFNVLMVHK RSHTGERPFQ
IK    RDQGSSALSG VGGIRLPNGK LKCDICGIVC IGPNVLMVHK RSHTGERPFQ
         151                                                  200
DAED  CNQCGASFTQ KGNLLRHIKL HSGEKPFKCP FCNYACRRRD ALTGHLRTHS
HEL   CNQCGRSFTQ KGNLLRHIKL HSGEKPFKCP FCSYACRRRD ALTGHLRTHS
AIO   CNQCGASFTQ KGNLLRHIKL HTGEKPFKCH LCNYACQRRD ALTGHLRTHS
IK    CNQCGASFTQ KGNLLRHIKL HSGEKPFKCH LCNYACRRRD ALTGHLRTHS
         201                                                  250
DAED  VSSPTVGKPY KCNYCGRSYK QQSTLEEHKE RCHNYLQSLS TDA..QALTG
HEL   .....VGKPH KCNYCGRSYK QRTSLEEHKE RCHNYLQNVS MEAAGQVMSH
AIO   .....VEKPY KCEFCGRSYK QRSSLEEHKE RCRAFLQNPD LGDAASV...
IK    .....VGKPH KCGYCGRSYK QRSSLEEHKE RCHNYLESMG LPGVCPVIKE
```

FIG. 1B-1

```
     251                                                        300
DAED Q..PGDEIRD LEMVPDSMLH .PSTERPTFI DRLANSLTKR KRSTPQKFVG
HEL  HVPPMEDCKE QEPIMDNNIS LVAFERPAVI EKLTANMGKR KSSTPQKFVG
AIO  EARHIK.... .AEM...... ..GSERALVL DRLASNVAKR KSSMPQKFIG
IK   ETNHNEMAED LCKI...... ..GAERSLVL DRLASNVAKR KSSMPQKFLG
     301                                                        350
DAED EKQMRFSLSD LPYDVNASGG YEKDVELVAH HGLEPGFGGS LAFVGTEHLR
HEL  EKLMRFSYPD IHFHMNLT.. YEKEAELMQS HMMDQAINNA ITYLGAEALH
AIO  EKRHCFD... ..ANYNPGYM YEKENEMMQT RMMDQAINNA ISYLGAEAFR
IK   DK..CLS... ..DMPYDSAN YEKE.DMMTS HVMDQAINNA INYLGAESLR
     351                                                        400
DAED PLRLPPTNCI SELTPVISSV YTQMQPIPSR LELPGSREAG EGPEDLGDGG
HEL  PLMQHAPSTI AEVAPVISSA YSQVYH.PNR IERPISRETS DSHENNMDGP
AIO  PLVQTPPAPT SEMVPVISSV YPIALTRAD. ....MP.... MGAPQEMEKK
IK   PLVQTPPG.S SEVVPVISSM YQLHKPPSD. ....GPPRSN HSAQDAVDNL
     401                                                        450
DAED PLLYRARGSL TDPGASPSNG CQDSTDTESN HEDRIGGVVS LPQGPPPQPP
HEL  TSLIRPKSRP QEREASPSNS CLDSTDSESS HDDR.....Q SYQGNPALNP
AIO  RILLPEKILP SERGLSPNNS AQDSTDTDSN HEDR.QHLYQ QSHVVLPQ..
IK   LLLSKAKSVS SEREASPSNS CQDSTDTESN AEEQRSGLIY LTNHINPH..
     451                                                        500
DAED PTIVVGRHSP AYAKEDPKPQ EGLLRGTPGP SKEVLRVVGE SGEPVKAFKC
HEL  KR....KQSP AYMKEDVKAL DA.TKAPKGS LKDIYKVFNG EGEQIRAFKC
AIO  .....ARNGM PLLKEVPRSF E.LLKPPPIC LRDSIKVINK EGEVMDVFRC
IK   .....ARNGL .ALKEEQRAY E.VLRAASEN SQDAFRVVST SGEQLKYYKC
     501                                                        550
DAED EHCRILFLDH VMFTIHMGCH GFRDPFECNI CGYHSQDRYE FSSHIVRGEH
HEL  EHCRVLFLDH VMYTIHMGCH GYRDPLECNI CGYRSQDRYE FSSHIVGGQH
AIO  DHCHVLFLDY VMFTIHMGCH GFRDPFECNM CGYRSHDRYE FSSHIARGEH
IK   EHCRVLFLDH VMYTIHMGCH GFRDPFECNM CGYHSQDRYE FSSHITRGEH
     551
DAED KVGSCRI
HEL  TFH--
AIO  RAMLK--
IK   RYHLS--
```

*FIG. 1B-2*

```
         1                                                          50
MDAED  ----------  ----------  --MESLFCES  SGDSSLEKEF  LGAPVGPSVS
XDAED  MSGSTFPTVV  GHKLESIFYS  STVAALDRPK  AGDSSLEKDF  SDALIGPTVS
         51                                                        100
MDAED  TPNSQHSSPS  RSLSANSIKV  EMYSDEESSR  LLGPDERLLD  KDDSVIVEDS
XDAED  TPNSRHSSPS  RSRSANSIKV  EMYGDDESGR  LLSHEDRLSE  KEDEIMGDDS
         101                                                       150
MDAED  LSEPLGYCDG  SGPEPHSPGG  IRLPNGKLKC  DVCGMVCIGP  NVLMVHKRSH
XDAED  LVEPLGYCDG  PGQDPHSP.G  ILLPNGKLKC  DICGMVCIGP  NVLMVHKRSH
         151                                                       200
MDAED  TGERPFHCNQ  CGASFTQKGN  LLRHIKLHSG  EKPFKCPFCN  YACRRRDALT
XDAED  TGERPFHCNQ  CGAPFTQKGN  LLRHIKLHSG  EKPFKCPFCN  YACRRRDALS
         201                                                       250
MDAED  GHLRTHSVSS  PTVGKPYKCN  YCGRSYKQQS  TLEEHKERCH  NYLQSLSTDA
XDAED  GHLRTHA...  ..VGKPYKCN  YCGRSYKQQN  TLEEHKERCH  NYLQSLSNEA
         251                                                       300
MDAED  QALTGQPGDE  IRDLEMVPDS  MLHPSTERPT  FIDRLANSLT  KRKRSTPQKF
XDAED  QHLPAHPG..  ....EWGPQG  ..........  .....GNCIC  TR...
         301                                                       350
MDAED  VGEKQMRFSL  SDLPYDVNAS  GGYEKDVELV  AHHGLEPGFG  GSLAFVGTEH
XDAED  ..EKQMRLSL  ADLPYEMNSS  ..FEKDVEIV  SHHPLDTAYG  NSLAFVG...
         351                                                       400
MDAED  LPL.RLPPTN  CISELTPVIS  SVYTQMQPIP  SRLELPGSRE  AGEGPEDLGD
XDAED  .GPMRLPPTN  CISEITPVIS  SVYTQLQPMQ  GRPDMPGNRE  AAEGHEDIPD
         401                                                       450
MDAED  GGPLLYRARG  SLTDPGASPS  NGCQDS.TDT  ESNHEDRIGG  VVSLPQGPPP
XDAED  GTQIHYRGR.  ...SEHGASPT NGCQDSNTDT  ESNHEERGSQ  ATS.......
         451                                                       500
MDAED  QPPPTIVVGR  HSPAYAKEDP  KPQEGLL...  .RGTPGPSKE  VLRVVGESGE
XDAED  ........SR  QSSAYAKEDQ  RPSDGGLLLP  SRSMPGTAKE  SLRVLGEDGV
         501                                                       550
MDAED  PVKAFKCEHC  RILFLDHVMF  TIHMGCHGFR  DPFECNICGY  HSQDRYEFSS
XDAED  QVKVFKCEHC  RVLFLDHVMF  TIHMGCHGFR  DPFECNICGY  HCQDRYEFSS
         551
MDAED  HIVRGEHKVG  SCRI
XDAED  HIVRGEHKV-  ----
```

*FIG. 1C*

METHOD OF IDENTIFYING A NEURAL PROGENITOR CELL BY EVALUATING EXPRESSION OF DAEDALOS

CROSS-REFERENCE TO RELATED APPLICATIONS

This application claims the benefit of U.S. Provisional Application Serial No. 60/243,110, filed on Oct. 25, 2000, the contents of which are incorporated herein by reference in their entirety.

FIELD OF THE INVENTION

The invention relates to the Daedalos nucleic acids, Daedalos polypeptides, and other related molecules and methods of making and using the same.

BACKGROUND OF THE INVENTION

The maintenance of tissues that require regeneration during the life of an organism is often achieved by the asymmetric division of a less differentiated stem cell to regenerate itself as well as give rise to a daughter cell that can then differentiate to repopulate the organ. The best characterized stem cells in the adult animal are those that regenerate the hematopoietic system. The production or proliferation of the hematopoietic stem cells (HSCs), and the subsequent expansion of progenitors with progressively restricted developmental potential derived from them, is regulated in part by members of the Ikaros gene family (Georgopoulos et al. (1997) Annu. Rev. Immunol. 15:155). Ikaros, Aiolos and Helios comprise the previously identified members of the Ikaros gene family. They encode conserved zinc finger DNA binding proteins which are expressed at varying levels in cells progressing through the hematopoietic lineages (Kelley et al. (1998) Curr. Biol, 8:508). Mutations in Ikaros cause defects in the hematopoietic stem cell as well as in later stages of lymphoid differentiation (Georgopoulos et al. (1994) Cell 79:143), while Aiolos mutations cause defects which are restricted to the lymphoid lineages, particularly in the sub-lineage that gives rise to B cells (Wang et al. (1998) Immunity 9:543).

Co-localization studies on the Ikaros family proteins suggest that these proteins bind to lineage specific genes in lymphoid cells and may serve to mediate rapid transitions between subsequently heritable repressed and active states in response to extrinsic signals. In support of this model, both Ikaros and Aiolos assemble into at least two distinct chromatin remodeling complexes (Kim et al. (1999) Immunity 10:345). One of these includes Mi-2 and histone deacetylase (HDAC) and can assemble chromatin in a closed conformation while the other includes members of a SWI/SNF complex associated with chromatin opening. Ikaros family proteins also regulate proliferative responses in maturing T cells, possibly by regulating access of the replication machinery to DNA (Avitahl et al. (1999) Immunity 10:333). These observations led to the general model that changes in the combinatorial expression of Ikaros family members during progression through the lymphoid lineage regulate the gene expression changes associated with successive steps in lymphoid development (Kelley et al. (1998) Curr. Biol. 8:508–515).

SUMMARY OF THE INVENTION

The invention is based, in part, on the discovery that Daedalos, a member of the Ikaros family of proteins, is differentially expressed at various stages of neural cell maturation. It was found that forced expression of Daedalos affected neural cell differentiation.

In general, the invention features a method of characterizing or detecting a cell, e.g., a neural cell, e.g., a neural progenitor cell, e.g., a neural progenitor cell in a cell sample. The method includes: providing a cell; and detecting the absence or presence of expression of Daedalos in the cell, wherein expression of Daedalos is indicative of a neural progenitor cell, to thereby characterize or detect a cell, e.g., a neural progenitor cell. The method can further include isolating or purifying the cell.

In one embodiment, the cell sample includes non-neural cells. The non-neural cells can be of any cell type. Non-neural cells can be included in the cell sample by extracting the cell sample from tissue of a subject, wherein the extraction results in a heterogeneous population of cells. Examples of non-neural cells that can be included in the cell sample are fibroblasts, epithelial cells, and hematopoietic cells. The method can be performed in vitro or in vivo.

In one embodiment, the absence or presence of a Daedalos mRNA is detected in the cell. Various techniques known to one of skill in the art can be used to detect a Daedalos mRNA. For example, a Daedalos mRNA can be detected by using a nucleic acid probe that hybridizes to a Daedalos mRNA. A detectable label, e.g., a radioactive or fluorescent label, can optionally be attached to the nucleic acid probe in this detection method. In another example, a Daedalos mRNA can be detected by PCR. Detection by PCR can include a further step of hybridization of a nucleic acid probe, e.g., a labeled nucleic acid probe, to the PCR product.

In one embodiment, the absence or presence of a Daedalos protein is detected. A Daedalos protein can be detected by various techniques known to one of skill in the art. For example, an antibody can be used that binds to a Daedalos protein. A detectable label, e.g., a radioactive or fluorescent label, can be attached to the antibody that binds to a Daedalos protein. Other known methods of protein detection include Western blot immunoassay, immunohistology, fluorescence activated cell sorting (FACS), radioimmunoassay (RIA), fluorescent immunoassay, enzyme linked immunosorbent assay (ELISA), or an immunoassay that uses a solid support, e.g., latex beads.

Expression of Daedalos can be used as a marker to characterize, detect, separate or purify cells.

In another embodiment, the method further includes separating the neural progenitor cell from at least one non-neural progenitor cell present in the cell sample. According to this method, the neural progenitor cell can be separated from other cells based upon expression of Daedalos detected in the neural progenitor cell.

In another embodiment, Daedalos expression is detected by providing a cell in which a Daedalos control region is functionally coupled to a nucleic acid which encodes a protein other than Daedalos, e.g., a reporter molecule, e.g., lacZ or a fluorescent product, e.g., green fluorescent protein. Expression can be used to follow development in a system, e.g., in a mouse, nematode, fish (e.g., a zebrafish), e.g., in a transgenic animal, e.g., a transgenic mouse, nematode or zebrafish.

In another aspect, the invention features a method of separating a neural progenitor cell from a cell population. The method includes: providing a cell population, e.g., two or more cells, containing a neural progenitor cell and a non-neural progenitor cell; evaluating expression of Daedalos in the neural progenitor cell and in the non-neural progenitor cell; and separating the neural progenitor cell from the non-neural progenitor cell based upon their expression of Daedalos. The cell population can be derived from neural tissue, e.g., glial cells. The cell population can contain neural and non-neural cells.

In one embodiment, the neural progenitor cell has a higher level of expression of Daedalos as compared to the non-neural progenitor cell.

In one embodiment, levels of Daedalos mRNA produced in the neural progenitor cell and in the non-neural progenitor cell are evaluated. Levels of Daedalos mRNA can be evaluated by various techniques known by one of skill in the art. In one example, levels of Daedalos mRNA are evaluated by a nucleic acid probe that hybridizes to the Daedalos mRNA. The nucleic acid probe can optionally include a detectable label attached to the nucleic acid probe. In another example, Daedalos mRNA is detected by PCR, as described herein. Additionally, Daedalos expression can be evaluated by detecting the level of Daedalos protein expression by the neural progenitor cell and the non-neural progenitor cell. In one example, the Daedalos protein is detected by an antibody that binds to the Daedalos protein. The antibody can optionally include a detectable label attached thereto. Other known methods of protein detection include Western blot immunoassay, immunohistology, fluorescence activated cell sorting (FACS), radioimmunoassay (RIA), fluorescent immunoassay, enzyme linked immunosorbent assay (ELISA), or an immunoassay that uses a solid support, e.g., latex beads.

In another aspect, the invention features a method of identifying the stage of neurogenesis of a cell. The method includes: providing a cell; evaluating the absence or presence of Daedalos expression in the cell; and identifying the stage of neurogenesis of the cell based upon the absence or presence of Daedalos expression in the cell.

In one embodiment, the cell is identified as a neural progenitor cell based upon the expression of Daedalos detected in the cell. For example, a high level of Daedalos expression detected in the cell can be used to identify the cell as a neural progenitor cell. In another example, the cell can be identified as a differentiated cell based upon the absence of Daedalos expression detected in the cell.

In one embodiment, the method further includes the step of isolating a first cell, based upon its stage of neurogenesis, from a second cell characterized by a different stage of neurogenesis.

The absence of presence of Daedalos expression in a cell can be evaluated by techniques known to those of skill in the art, as described herein. For example, the level of Daedalos mRNA produced in the cell can evaluated, e.g., using a nucleic acid probe and/or by PCR analysis. In another example, the level of Daedalos expression can be evaluated by detecting a Daedalos protein produced by the cell. A Daedalos protein can be detected by using an antibody, e.g., an antibody having a detectable label attached thereto or other known methods described herein. Expression can be evaluated by detecting the expression of a reporter product, e.g., a lacZ or a fluorescent product such as GFP, under the control of a Daedalos regulatory region.

In another aspect, the invention features a method of maintaining a cell, e.g., a neural progenitor cell or neural stem cell, in a non-differentiated state, or inhibiting differentiation of a cell, e.g., a neural progenitor cell or neural stem cell. The method includes: modulating, e.g., increasing Daedalos activity or expression, to thereby maintain a cell in a non-differentiated state. Expression of Daedalos can be increased by various techniques. A compound can optionally be provided to the cell that causes increased expression of Daedalos. Examples of compounds that can cause increased expression of Daedalos include: (1) a Daedalos polypeptide, fragment, or analog thereof; (2) a nucleic acid encoding a Daedalos polypeptide, fragment, or analog thereof; and (3) an agent that increases expression of the endogenous Daedalos gene of the cell. Nucleic acids according to example (2) can contain mRNA, cDNA, and/or genomic DNA. Nucleic acids can include all or a portion of the Daedalos coding region, regulatory sequences, such as a promoter, e.g., derived from the Daedalos gene or from another gene, and an enhancer, e.g., derived from the Daedalos gene or from another gene. Agents according to example (3) can cause an increase in expression of the endogenous Daedalos gene of the cell. Agents may increase expression of the endogenous Daedalos gene either directly or indirectly, e.g., by binding to the promoter of the Daedalos gene or another gene, or by altering the regulatory sequence the Daedalos gene or another gene.

Examples of agents that can increase expression of Daedalos include: a Daedalos polypeptide or a functional fragment or analog thereof; a peptide or protein agonist of Daedalos that increases the activity of Daedalos (e.g., by increasing or stabilizing Daedalos association with a Daedalos binding partner, e.g., DNA or another Ikaros family member, or by increasing nuclear translocation of Daedalos); a small molecule that increases expression of Daedalos, e.g., by binding to the promoter region of the Daedalos gene; an antibody, e.g., an antibody that binds to and stabilizes or assists the binding of Daedalos to a Daedalos binding partner (e.g., DNA or another DNA binding protein, e.g., homo or heterodimerization between Daedalos and Ikaros, Aiolos or Helios factor); or a nucleotide sequence encoding a Daedalos polypeptide or functional fragment or analog thereof. The nucleotide sequence can be a genomic sequence or a cDNA sequence. The nucleotide sequence can include: a Daedalos coding region; a promoter sequence, e.g., a promoter sequence from a Daedalos gene or from another gene; an enhancer sequence; untranslated regulatory sequences, e.g., a 5' untranslated region (UTR), e.g., a 5'UTR from a Daedalos gene or from another gene, a 3' UTR, e.g., a 3'UTR from a Daedalos gene or from another gene; a polyadenylation site; an insulator sequence. In another preferred embodiment, the level of Daedalos protein is increased by increasing the level of expression of an endogenous Daedalos gene, e.g., by increasing transcription of the Daedalos gene or increasing Daedalos mRNA stability. In a preferred embodiment, transcription of the Daedalos gene is increased by: altering the regulatory sequence of the endogenous Daedalos gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Daedalos gene to be transcribed more efficiently.

In a preferred embodiment, Daedalos expression or activity is increased in the presence of neural growth factor, e.g., exogenous or endogenous neural growth factor.

In another aspect, the invention features a method of determining if a subject is at risk for a neural cell related disorder. The method includes: evaluating expression of Daedalos in a cell of the subject; and determining the subject's risk for a neural cell related disorder based upon the absence or presence of expression of Daedalos in the cell. In this method, expression of Daedalos can be evaluated in a cell sample derived from neural tissue.

In one example, the neural cell related disorder is a proliferative disorder, e.g., cancer.

According to the method, a subject can be determined to be at risk for a neural cell related disorder based upon an increased expression of Daedalos in the cell of the subject, as compared to the level of expression of Daedalos in a cell of a subject not at risk. When evaluating expression of Daedalos in the cell of the subject, a comparison of expression levels can be made to a cell of the same type, e.g., a neural cell, derived from a healthy individual, e.g., an individual not believed to be at risk for or to have a neural cell related disorder. Expression of Daedalos in the cell of the subject can be evaluated by using techniques known to those of skill in the art, as described herein, e.g., detection of Daedalos mRNA and/or protein.

In another aspect, the invention features a method of controlling cell differentiation. The method includes: providing a cell; and modulating expression of Daedalos in the cell, to thereby control differentiation of the cell. Expression of Daedalos in a cell can be modulated either in vitro or in vivo.

In one embodiment, the cell is a neural progenitor cell.

In one embodiment, modulating expression of Daedalos can control the neural differentiation of the cell, e.g., a neural progenitor cell.

In one embodiment, expression of Daedalos is increased. Increasing Daedalos expression can affect the differentiation and/or proliferation of the cell, e.g., increased expression of Daedalos can inhibit neural cell differentiation. Expression of Daedalos can be increased by various techniques known to one of skill in the art. A compound can optionally be provided to the cell that causes increased expression of Daedalos. Examples of compounds that can cause increased expression of Daedalos include: (1) a Daedalos polypeptide, fragment, or analog thereof; (2) a nucleic acid encoding a Daedalos polypeptide, fragment, or analog thereof; and (3) an agent that increases expression of the endogenous Daedalos gene of the cell. Nucleic acids according to example (2) can contain mRNA, cDNA, and/or genomic DNA. Nucleic acids can include all or a portion of the Daedalos coding region, regulatory sequences, such as a promoter, e.g., derived from the Daedalos gene or from another gene, and an enhancer, e.g., derived from the Daedalos gene or from another gene. Agents according to example (3) can cause an increase in expression of the endogenous Daedalos gene of the cell. Agents may increase expression of the endogenous Daedalos gene either directly or indirectly, e.g., by binding to the promoter of the Daedalos gene or another gene, or by altering the regulatory sequence the Daedalos gene or another gene.

In another embodiment, a compound is provided to the cell that causes decreased expression of Daedalos. Decreasing Daedalos expression can affect the differentiation and/or proliferation of the cell, e.g., decreasing expression of Daedalos can promote neural cell differentiation. Expression of Daedalos can be decreased by various techniques known to one of skill in the art. A compound can optionally be provided to the cell that causes decreased expression of Daedalos. In one example, a compound causes a decrease in Daedalos expression by binding to a Daedalos nucleic acid sequence, e.g., a compound such as an antisense nucleic acid or a ribozyme that binds to a Daedalos mRNA. In another example, a compound causes a decrease in Daedalos expression by binding to a Daedalos polypeptide, e.g., a compound such as an antibody, small molecule, or a peptide. In another example, a compound causes a decrease in Daedalos expression by reducing expression of the endogenous Daedalos gene in the cell, e.g., a compound such as a small molecule, peptide, or nucleic acid that binds to the promoter or regulatory sequence of the Daedalos gene. In another embodiment, the compound can decrease Daedalos expression by, e.g., by binding to Daedalos and playing a dominant negative role. For example, the compound can be a Daedalos polypeptide or other polypeptide (e.g., an Ikaros, Helios or Aiolos polypeptide) which can form a dimer, e.g., a homo or heterodimer with Daedalos but that interferes with Daedalos DNA binding and/or transcriptional activity. Such polypeptide can include Ikaros, Helios, Aiolos or Daedalos polypeptides in which one or more of the N-terminal zinc fingers has been removed.

In another aspect the invention features a method of obtaining a population of neural progenitor cells. The method includes: providing a cell sample comprising at least one neural progenitor cell; and increasing the level of Daedalos in the cell sample. Increasing Daedalos expression can affect the differentiation and/or proliferation of the cell, e.g., increasing proliferation of the neural progenitor cell and/or inhibiting the differentiation of the neural progenitor cell. The level of Daedalos in the cell sample can be increased in vitro or in vivo. Additional compounds can be added to the neural progenitor cell that affect its proliferation, differentiation, and/or survival. For example, the level of growth factors, e.g., FGF-2 and/or EGF, provided to the neural progenitor cell can be increased.

In a preferred embodiment, the level of Daedalos can be increased by administering to the cell an agent that increases Daedalos expression (e.g., by increasing Daedalos transcription rate or mRNA half-life), protein levels, or activity. The agent can be, e.g., a Daedalos polypeptide or a functional fragment or analog thereof; a peptide or protein agonist of Daedalos that increases the activity of Daedalos (e.g., by increasing or stabilizing Daedalos association with a Daedalos binding partner, e.g., DNA or another Ikaros family member, or by increasing nuclear translocation of Daedalos); a small molecule that increases expression of Daedalos, e.g., by binding to the promoter region of the Daedalos gene; an antibody, e.g., an antibody that binds to and stabilizes or assists the binding of Daedalos to a Daedalos binding partner (e.g., DNA or another DNA binding protein, e.g., homo or heterodimerization between Daedalos and Ikaros, Aiolos or Helios factor); or a nucleotide sequence encoding a Daedalos polypeptide or functional fragment or analog thereof. The nucleotide sequence can be a genomic sequence or a cDNA sequence. The nucleotide sequence can include: a Daedalos coding region; a promoter sequence, e.g., a promoter sequence from a Daedalos gene or from another gene; an enhancer sequence; untranslated regulatory sequences, e.g., a 5' untranslated region (UTR), e.g., a 5'UTR from a Daedalos gene or from another gene, a 3' UTR, e.g., a 3'UTR from a Daedalos gene or from another gene; a polyadenylation site; an insulator sequence. In another preferred embodiment, the level of Daedalos protein is increased by increasing the level of expression of an endogenous Daedalos gene, e.g., by increasing transcription of the Daedalos gene or increasing Daedalos mRNA stability. In a preferred embodiment, transcription of the Daedalos gene is increased by: altering the regulatory sequence of the endogenous Daedalos gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Daedalos gene to be transcribed more efficiently.

In another aspect, the invention features a method of obtaining a population of neural cells. The method includes: providing a cell sample comprising a neural progenitor cell; and inhibiting the expression or activity of Daedalos in the neural progenitor cell, to thereby obtain neural cells. Inhibiting the expression or activity of Daedalos can affect the differentiation and/or proliferation of the cell, e.g., it can result in the differentiation of the neural progenitor cell.

In one embodiment, a compound is provided to the neural progenitor cell that causes decreased expression or activity of Daedalos. For example, the compound can cause a decrease in Daedalos expression by binding to a Daedalos nucleic acid sequence, e.g., a compound that binds to a Daedalos mRNA such as an antisense nucleic acid or a ribozyme. In another example, the compound causes a decrease in Daedalos expression or activity by binding to a Daedalos polypeptide, e.g., any such polypeptide described herein. In another example, the compound can cause a decrease in Daedalos expression by reducing expression of the endogenous Daedalos gene in the cell.

In a preferred embodiment, Daedalos expression, levels, or activity is decreased by administering to the cell an agent that decreases Daedalos expression, levels or activity. In a preferred embodiment, the agent that inhibits Daedalos levels and/or activity can be one or more of: a Daedalos binding protein, e.g., a soluble Daedalos binding protein that binds and inhibits a Daedalos activity, e.g., DNA binding activity, nuclear translocation activity, homo or heterodimerization activity, or transcriptional activation activity; an antibody that specifically binds to the Daedalos protein, e.g., an antibody that disrupts Daedalos's ability to bind DNA or another transcription factor, to translocate to the nucleus, or bind DNA; a mutated inactive Daedalos or fragment thereof which, e.g., binds to a Daedalos binding partner (e.g., DNA or another transcription factor, e.g., Ikaros, Aiolos or Helios factor) but disrupts a Daedalos activity, e.g., nuclear translocation activity or transcriptional activation activity; a Daedalos nucleic acid molecule that can bind to a cellular Daedalos nucleic acid sequence, e.g., mRNA, and inhibit expression of the protein, e.g., an antisense molecule or Daedalos ribozyme; an agent which decreases Daedalos gene expression, e.g., a small molecule which binds the promoter of Daedalos and decreases Daedalos gene expression. In another preferred embodiment, Daedalos is inhibited by decreasing the level of expression of an endogenous Daedalos gene, e.g., by decreasing transcription of the Daedalos gene. In a preferred embodiment, transcription of the Daedalos gene can be decreased by: altering the regulatory sequences of the endogenous Daedalos gene, e.g., by the addition of a negative regulatory sequence (such as a DNA-biding site for a transcriptional repressor), or by the removal of a positive regulatory sequence (such as an enhancer or a DNA-binding site for a transcriptional activator).

In another aspect, the invention features a method of treating a neural cell related disorder. The method includes: providing a subject having a neural cell related disorder; and modulating expression of Daedalos in a cell of the subject, to thereby treat the disorder. The neural cell related disorder can be a neurodegenerative disease, e.g., Parkinson's disease, Alzheimer's disease, ischemic damage such as stroke or spinal chord trauma, epilepsy, or multiple sclerosis.

In a preferred embodiment, Daedalos expression, protein level, or activity is increased to thereby treat the disorder, e.g., a disorder characterized by insufficient proliferation or aberrant differentiation of a Daedalos responsive cell. Daedalos expression, protein level, or activity can be increased by administering to the cell an agent that increases Daedalos expression (e.g., by increasing Daedalos transcription rate or mRNA half-life), protein levels, or activity. The agent can be, e.g., a Daedalos polypeptide or a functional fragment or analog thereof; a peptide or protein agonist of Daedalos that increases the activity of Daedalos (e.g., by increasing or stabilizing Daedalos association with a Daedalos binding partner, e.g., DNA or chromatin, or by increasing nuclear translocation of Daedalos); a small molecule that increases expression of Daedalos, e.g., by binding to the promoter region of the Daedalos gene; an antibody, e.g., an antibody that binds to and stabilizes or assists the binding of Daedalos to a Daedalos binding partner (e.g., another DNA binding protein or DNA); or a nucleotide sequence encoding a Daedalos polypeptide or functional fragment or analog thereof. The nucleotide sequence can be a genomic sequence or a cDNA sequence. The nucleotide sequence can include: a Daedalos coding region; a promoter sequence, e.g., a promoter sequence from a Daedalos gene or from another gene; an enhancer sequence; untranslated regulatory sequences, e.g., a 5' untranslated region (UTR), e.g., a 5'UTR from a Daedalos gene or from another gene, a 3' UTR, e.g., a 3'UTR from a Daedalos gene or from another gene; a polyadenylation site; an insulator sequence. In another preferred embodiment, the level of Daedalos protein is increased by increasing the level of expression of an endogenous Daedalos gene, e.g., by increasing transcription of the Daedalos gene or increasing Daedalos mRNA stability. In a preferred embodiment, transcription of the Daedalos gene is increased by: altering the regulatory sequence of the endogenous Daedalos gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Daedalos gene to be transcribed more efficiently.

In another embodiment, Daedalos expression, protein levels or activity is decreased to thereby treat the disorder, e.g., a proliferative disorder. In a preferred embodiment, Daedalos expression, levels, or activity is decreased by administering to the cell an agent that decreases Daedalos expression, levels or activity. In a preferred embodiment, the agent that inhibits Daedalos levels and/or activity can be one or more of: a Daedalos binding protein, e.g., a soluble Daedalos binding protein that binds and inhibits a Daedalos activity, e.g., chromatin binding activity, nuclear translocation activity, DNA binding activity, or transcriptional activation activity; an antibody that specifically binds to the Daedalos protein, e.g., an antibody that disrupts Daedalos's ability to bind a binding partner described herein, to translocate to the nucleus, or bind DNA; a mutated inactive Daedalos or fragment thereof which, e.g., binds to a Daedalos binding partner but disrupts a Daedalos activity, e.g., nuclear translocation activity or transcriptional activation activity; a Daedalos nucleic acid molecule that can bind to a cellular Daedalos nucleic acid sequence, e.g., mRNA, and inhibit expression of the protein, e.g., an antisense molecule or Daedalos ribozyme; an agent which decreases Daedalos gene expression, e.g., a small molecule which binds the promoter of Daedalos and decreases Daedalos gene expression. In another preferred embodiment, Daedalos is inhibited by decreasing the level of expression of an endogenous Daedalos gene, e.g., by decreasing transcription of the Daedalos gene. In a preferred embodiment, transcription of the Daedalos gene can be decreased by: altering the regulatory sequences of the endogenous Daedalos gene, e.g., by the addition of a negative regulatory sequence (such as a DNA-biding site for a transcriptional repressor), or by the removal of a positive regulatory sequence (such as an enhancer or a DNA-binding site for a transcriptional activator).

As used herein, "treatment" or "treating a subject" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, a symptoms of the disease or the predisposition toward disease. A therapeutic agent includes, but is not limited to, small molecules, peptides, antibodies, ribozymes and antisense oligonucleotides.

In one embodiment, the neural cell related disorder is characterized by insufficient neural cell differentiation.

In another embodiment, the neural cell related disorder is characterized by unwanted or excessive neural cell differentiation.

In one embodiment, the neural cell related disorder is a neural cell proliferative disorder, e.g., cancer, e.g., neuroma.

In one embodiment, the level of Daedalos in the cell of the subject is increased. Increasing the level of Daedalos in the cell of the subject can result in increased neural cell differentiation.

In one embodiment, the level of Daedalos in the cell of the subject is decreased. Decreasing the level of Daedalos in the cell of the subject can result in decreased neural cell differentiation.

In another aspect, the invention features a method of neural cell culture. The method includes: providing a neural cell in vitro; and modulating expression of Daedalos in the neural cell, to thereby provide a neural cell culture.

In one embodiment, the method includes increasing the expression of Daedalos in the neural cell.

In another embodiment, the method includes decreasing the expression of Daedalos in the neural cell.

A "progenitor cell", as used herein, is a cell that can divide to give rise to two cells, wherein the progenitor cell differs in its stage of maturation from at least one of the two cells.

A "neural cell" is a cell having one or more features of a cell of the neural lineage. The term "neural cell" includes all cells of the neural lineage, regardless of their stage of maturation.

A "neural progenitor cell" is a progenitor cell of the neural cell lineage, e.g., a cell that does not proliferate and/or differentiate to give rise to a non-neural cell under normal in vivo conditions.

A "cell sample" is a collection of two or more cells. A cell sample can be provided in any form, e.g., in a vessel, e.g., in a tube. The cell sample can contain cells derived from neural tissue of a subject. In one example, the cell sample also contains non-neural progenitor cells, e.g., differentiated neural cells.

A "differentiated neural cell" is a neural cell that cannot divide to give rise to a daughter cell that differs in its stage of maturation from the differentiated neural cell. A "differentiated neural cell" is also referred to as an end-stage cell.

A "control region" of a gene is a transcriptional regulatory element or combination of regulatory elements. For example, a control region of a Daedalos gene can be a promoter or functional fragment thereof, an enhancer sequence, an insulator sequence, or combinations thereof.

All publications and patents referred to herein are incorporated by reference.

Other features and advantages of the invention will be apparent from the following detailed description, and from the claims.

BRIEF DESCRIPTION OF THE DRAWINGS

FIG. 1A is a schematic of the Ikaros family proteins, indicating the zinc finger domains (dark boxes) that confer sequence specific DNA binding properties or mediate dimerization, as well as additional regions of homology between all four proteins (gray boxes).

FIG. 1B depicts the predicted amino acid sequence of Daedalos (Daed; SEQ ID NO:1), aligned with the other Ikaros gene family members, Helios (Hel; SEQ ID NO:2), Aiolos (Aio; SEQ ID NO:3), and Ikaros (Ik; SEQ ID NO:4). Residues conserved in Ikaros family members are highlighted in gray and the zinc finger domains are boxed.

FIG. 1C depicts the amino acid sequence of the Xenopus Daedalos (xDaed; SEQ ID NO:5) protein, aligned with the amino acid sequence of the mouse Daedalos (mDaed) protein (SEQ ID NO:1).

DETAILED DESCRIPTION OF THE INVENTION

Overview

Figure 2A:
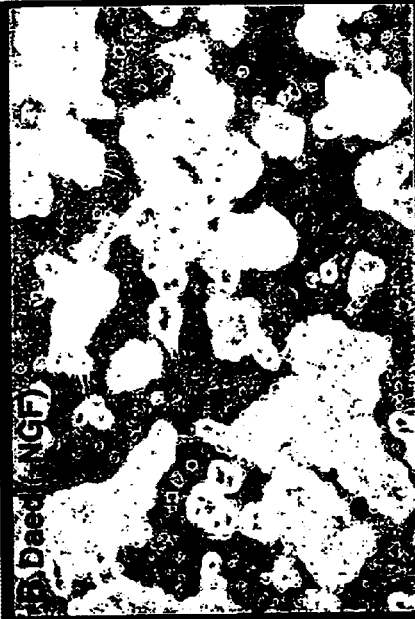
FIG. 2A depicts subcloned stable transfectants of PC12 cells harboring a control expression vector.

Ikaros, and the related proteins Aiolos and Helios, regulate the development and differentiation of the hematopoietic stem cell (HSC) and its progeny in the lymphoid lineage. Daedalos, another member of the Ikaros gene family, is transiently expressed in the developing central nervous system (CNS) and is downregulated upon terminal differentiation. Expression of Daedalos was also observed in regions of the adult brain that harbor neural stem cells. Forced expression of Daedalos in the Xenopus embryo did not affect specification of the neurogenic region but prevented neuronal differentiation. The neuronal differentiation of PC12 cells in response to NGF was also blocked by forced expression of Daedalos. However, no effects on the behavior of PC12 cells were observed when they are maintained as cycling populations.

Cloning of the Daedalos cDNA

A fourth member of the Ikaros gene family, designated Daedalos, was cloned using PCR with degenerate primers (Morgan et al. (1997) EMBO J 16:2004; Honma et al. (1999) FEBS Letters 447:76). PCR amplification was performed as follows. 40 cycles (95°, 30 seconds; 45°, 1.5 minutes; 72°, 2 minutes) were carried out in a Pfu buffer containing 3 mM $MgSO_4$, using degenerate primers designed from conserved regions of the murine Ikaros family of proteins: DEG 10 (TG (T/C)AA(T/C)CA(A/G)TG(T/C)GGIGCI (T/A)CITT(T/C)AC; SEQ ID NO:6) and DEG 12 (TG(G/A)CAICCCAT(G/A)TGIATIGT (G/A)(T/A)ACAT; SEQ ID NO:7). This resulted in the amplification of a 900 base pair product. 3' and 5' RACE (Marathon, Promega) were employed to clone the remaining coding sequences for each transcript as well as the 5' and 3' UTRs.

Daedalos cDNAs encode a protein highly homologous to the other Ikaros family members. The four N-terminal zinc fingers that mediate DNA binding and the two C-terminal fingers required for homo and heterodimerization between family members (Sun et al. (1996) EMBO J 15:5358) are nearly identical in all four proteins (FIGS. 1A and 1B). Several other domains shared between Ikaros, Aiolos and Helios are conserved in Daedalos as well, although Daedalos is less similar to the other three than they are to each other (FIG. 1B).

Expression Patterns of Daedalos

In situ analysis performed during mouse embryogenesis revealed that Daedalos is the first member of the Ikaros family whose expression is detected in the neural plate at moderate levels by Day 7.5 of gestation. In contrast, Daedalos is not detected at similar levels until Day 11 of gestation, at which time it is expressed in the rostral neural tube and spreads caudally as the spinal chord develops. A cross-sectional view through the neural tube reveals that Daedalos expression is highest in cells that have migrated from the ventricular zone. In late gestation, Daedalos expression was detected in much of the developing CNS, but expression declined in most regions shortly after birth. In addition to expression in the CNS, Daedalos was also detected by in situ hybridization in some neural crest derivatives during embryogenesis, including a subset of cells in the developing dorsal root ganglia (DRGs) and adrenal medulla. Consistent with this pattern of expression in vivo, Daedalos mRNA was also detected in melanocyte cell lines and in PC12 and n-tera 2 cells which have neurogenic potential.

This pattern of expression during embryogenesis suggests a function for Daedalos in neurogenesis. Features of the Daedalos expression pattern in the adult CNS support this conclusion and suggest Daedalos expression identifies a persisting progenitor population. Expression is maintained in regions of the adult brain where neurogenesis continues throughout adult life (Luskin et al. (1993) Neuron 11: 173; Palmer et al. (1997) Mol. Cell. Neurosci. 8:389), including the dentate gyrus of the hippocampus and the periventricular region of the forebrain which gives rise to interneurons that populate the olfactory bulb. Daedalos expression was detected in the ependymal layer lining the ventricles and in the adjacent subependymal zone, regions from which neural stem cells have been isolated in the adult (Chiasson et al. (1999) J. Neuroscience 19:4462; Corotto (1993) Neurosci Letter 149:111; Johansson et al. (1999) Cell 96:25). While it is uncertain whether neural stem cells reside in the ependymal region, the subependymal zone, or both, in vivo (Temple (1999) Curr. Biol. 9:R397), the expression of Daedalos in a subset of these cells could identify either neural stem cells or their recently generated progeny.

The expression patterns of the Ikaros family in the nervous system is formally analogous to that observed in the hematopoietic system, where differential expression of the family members occurs as cells proceed through the lineages, regulating expansion and differentiation of progressively committed progenitors (Kelley et al. (1998) Curr Biol. 8:508). In the nervous system, Daedalos expression was found to correlate with an intermediate step in neurogenesis, first appearing after neural plate formation, then predominating in cells that have migrated from the periventricular regions, and expression ultimately being extinguished in regions where terminal differentiation has occurred. This expression pattern suggests one or more of the following possibilities: (1) Daedalos expression is activated as a consequence of progression down the neural lineage; (2) Daedalos expression contributes to the maintenance of neural progenitors in an undifferentiated state; and (3) the subsequent suppression of Daedalos expression is required for terminal differentiation to occur.

Modulation of Daedalos Expression in vitro

To test these possibilities described above directly, two types of experiments were performed, the effects of which were measured: (1) ectopically expressing Daedalos mRNA in a cell; and (2) maintaining the expression of Daedalos in a cell after the time when its expression would normally be extinguished.

Injection of RNA into Xenopus embryos was performed to alter Daedalos expression. Spatially restricted expression of transcription factors confers neurogenic potential on dorsal ectoderm, and a hierarchy of transcription factors, influenced by Notch-mediated lateral inhibition, dictates the neuronal differentiation of a subset of these cells. The expression of neurogenin-lb (Ma et al. (1996) Cell 87:43) and xDelta-1 (Chitnis et al. (1995) Nature 375:761) serve as markers of successive steps in neural commitment while expression of neuron specific tubulin 25 (n-tubulin) identifies differentiating neurons (Chitnis (1999) Curr. Opinion Neurobiol. 9:18).

Partial cDNAs derived from a Xenopus orthologue of Daedalos were cloned by PCR with degenerate primers. The cDNA ends were then identified by RACE, which provided the requisite information for subsequent recloning of the entire coding region from Xenopus embryo mRNA (FIG. 1C). 80% of the residues in the Xenopus Daedalos protein are identical to those in the mouse Daedalos protein, although some regions of the mouse protein are absent in the Xenopus protein (FIG. 1C). While the functional significance of these absent regions has not been explored, they correspond to segments of the mouse Daedalos that are not conserved among other murine paralogues.

PCR analysis of Daedalos transcripts confirmed that they are expressed from stage 11 while primary neurogenesis is occurring. Total RNA was prepared from 100 Xenopus laevis embryos at stage 11 or 12 and 2 micrograms were reverse transcribed. 165 nanograms of cDNA products (16.5 ng for histone H-4) were amplified in the presence of 1.5 $\mu$Ci each of [P32] dATP and [P32] dCTP using the following primer pairs: histone H-4 (20 cycles, using primers 5'-AGGGACAACATCCAGGGCATCACG (SEQ ID NO:8) and 3'-ATCCATGGCGGTAACGGTCTTCCT (SEQ ID NO:9)); XDaedalos (31 cycles, using primers 5'-ATTCTGTAACTACGCTTGTCGTCG (SEQ ID NO:10) and 3'-AACAATIGCCATAAGCAGTGTCCA (SEQ ID NO:11)); and neurogenin-lb (28 cycles, using primers 5'-CATATTGGTACAGGACTCCTATGC (SEQ ID NO:12) and 3'-CTTGACCCTTATGGGAAGCAGGAA (SEQ ID NO: 13)). The number of cycles employed were in the range for linear amplification of each target. The products were separated on a 5% polyacrylamide gel and quantitated on a phosphoimager (Molecular Dynamics). Input cDNA levels were corrected to achieve similar histone H-4 content.

For these experiments, capped mRNA was prepared using the mMessage mMachine (Ambion) and linearized templates for b-gal or full length Xenopus Daedalos coding sequence in the RN3 vector. Approximately 50 pg per embryo were injected in a volume of 6 nl.

Injection of RNA encoding Xenopus Daedalos into Xenopus embryos at the two cell stage did not result in any ectopic expression of either n-tubulin (n=100) or the earlier markers of the neurogenic lineage, neurogenin 1b (n=47) or Delta-1 (n=47), in cells normally fated to become lateral ectoderm. Thus, Daedalos was found to be insufficient to convert presumptive epidermis to a neurogenic fate.

The maintenance of Daedalos expression within the neurogenic region was found to lead to unilateral suppression of neuronal differentiation, which was revealed by suppression of n-tubulin expression. N-tubulin expression was repressed in cells containing injected RNA. These cells were identified by detection of the activity encoded by co-injected b-galactosidase (b-gal) mRNA. Reduced n-tubulin expression was not observed in embryos injected with b-gal tracer alone. Although Daedalos consistently repressed the expression of this terminal differentiation marker, both neurogenin-1b and Delta-1 transcripts could be found in cells harboring the exogenous Daedalos mRNA in both day 61 and day 73 embryos. While the expression of these markers was normal in the majority of the injected embryos, there were some alterations of their expression patterns in many of the injected embryos. 38% of the injected embryos showed some alteration of neurogenein expression, while 50% of the injected embryos showed some difference in expression of Delta-1 between the injected and uninjected sides. The normal expression patterns of these markers are quite dynamic and they are sensitive indicators of alterations in developmental rate. While forced expression of Daedalos does not prevent expression of these neurogenic markers, the variable effects on their expression in some cells may reflect interference with, or abnormal progression through, early steps in the neural lineage caused by heterochronic or overexpression of Daedalos in these cells.

These results suggest that Daedalos expression does not dictate a pro-neural fate but rather is activated as a consequence of the adoption of that fate. Furthermore, it suggests that the down regulation of Daedalos expression, normally observed during neuronal differentiation, is a required step in this process. To investigate this possibility further, the effects of forced Daedalos expression in a pheochromocytoma cell line, PC12, were examined. These cells can be maintained as an undifferentiated proliferating population, possessing characteristics of adrenal chromaffin cells. Alternatively, PC12 cells can be induced by the addition of NGF to the culture media to undergo differentiation to a cell type having neuronal characteristics (Greene et al. (1976) Proc. Natl. Acad. Sci. USA 73:2424). Thus PC12 may be used to assess the effects of maintained Daedalos expression on this specific step in neuronal differentiation. Similar to what was observed with both neural progenitors and adrenal chromaffin cells in vivo, PC12 cells express Daedalos mRNA when maintained in growth media. In these experiments, PC12 cells ($1 \times 10^5$ cells/well) were seeded on laminin-coated 12-well dishes (Sumitomo Bakelite Co., Akita, Japan) and cultured with DMEM (Gibco BRL, 23700-040) supplemented with 5% fetal bovine serum (Sanko Junyaku Co., Tokyo, Japan) and 5% horse serum (Gibco BRL). Neurite induction was induced by addition of 25 ng/ml of NGF (Sigma).

Figure 2B:
FIG. 2B depicts subcloned stable transfectants of PC12 cells harboring a Daedalos expression vector.
Figure 2C:
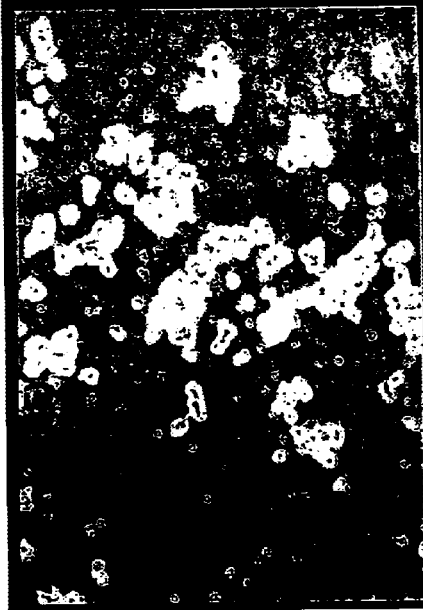
FIG. 2C depicts subcloned stable transfectants of PC12 cells harboring a control expression vector and cultured for two weeks in media supplemented with NGF.
Figure 2D:
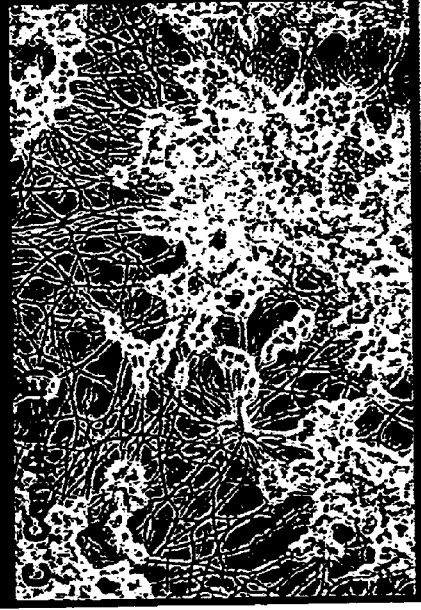
FIG. 2D depicts subcloned stable transfectants of PC12 cells harboring a Daedalos expression vector and cultured for two weeks in media supplemented with NGF.

PC12 cells were subcloned to generate more homogeneous populations and were then transfected with either (1) a plasmid containing the coding sequences of Daedalos driven by a constitutively active promoter or (2) a vector alone. Four independent lines for each treatment were subcloned under growth conditions on selective media, and the increased expression of Daedalos mRNA in lines harboring the Daedalos expression construct was confirmed by Northern hybridization. No difference in the frequency of recovered clones or their rate of growth was observed between the experimental and control populations and the morphology of clones expressing the transfected Daedalos cDNA was indistinguishable from controls in growth media (FIGS. 2A and 2B). Thus, forced expression of Daedalos had no discernible effect on these cells while they are maintained as proliferating "progenitors". However, after 3 days in culture in media containing NGF, the control cell populations had extended an extensive arbor of neurites, while the Daedalos expressing subclones had few if any neurites after 3 days and failed to develop them over an additional 2 weeks in culture (FIGS. 2C and 2D). Thus, the repression of Daedalos expression that normally occurs during neuronal differentiation appears to be a necessary step for the conversion to a neuronal morphology in the PC12 cell line.

Methods of Detection

The invention provides methods for detecting a neural cell based upon the cell's expression of Daedalos. Daedalos has been shown to be expressed at significant levels in neural progenitor cells and to be absent or expressed at reduced levels in differentiated neural cells. By exploiting these expression patterns of Daedalos, methods can be devised for the detection of neural cells.

In one embodiment, Daedalos is detected in a cell sample, thereby permitting the identification of the cell sample as containing a neural progenitor cell and/or as containing committed neural cells. The cell sample can be analyzed in vitro or in vivo and the cell sample can be derived from any of the body's tissues, e.g., neural tissue. The cell sample can include neural and/or non-neural cells.

Daedalos expression can be detected by a variety of techniques known in the art. For example, Daedalos mRNA produced by a cell can be detected by, e.g., hybridization techniques or by PCR. Either of these techniques can use a detectable label attached to a nucleic acid probe. Additionally, Daedalos protein produced by a cell can be detected by, e.g., using an antibody, optionally including a detectable label, that binds to the Daedalos protein.

These methods of detection can be extended to include methods of separating one cell type from another based upon the presence or absence of Daedalos expression. For example, a neural progenitor cell can be identified based upon its expression of Daedalos and can then be separated from other cells in a cell sample having reduced Daedalos expression. This allows for the separation of a neural progenitor cell from other cell types such as differentiated or committed neural cells and non-neural cells.

In another embodiment, the invention provides methods of identifying the stage of neurogenesis of a cell based upon the cell's expression of Daedalos. For example, a cell can be identified as a neural progenitor cell based upon its expression of Daedalos. A cell can be identified as a neural progenitor by either the presence of Daedalos in the cell or by the presence of levels of Daedalos in the cell that are elevated as compared to non-neural progenitor cell populations. In another example, a cell can be identified as a non-neural progenitor cell, e.g., a differentiated or committed cell, based upon its expression of Daedalos. A cell can be identified as a non-neural progenitor cell by either the absence of Daedalos in the cell or by the presence of levels of Daedalos in the cell that are reduced as compared to neural progenitor cells. Expression of Daedalos can be evaluated by methods described herein, e.g., by analysis of Daedalos mRNA or protein. The methods can further include steps of isolating one cell from another based upon their differing stages of neurogenesis.

Methods of Separation

Another aspect of the invention relates to methods of separating cells based upon their expression of Daedalos. These methods can be used to separate neural cell populations, e.g., neural progenitor cells, from other cell populations. For example, in a cell population containing both neural progenitor cells and non-neural progenitor cells, expression of Daedalos can be evaluated and the cells can be divided based upon their expression of Daedalos. In this example, the neural progenitor cell has a higher level of Daedalos expression than does the non-neural progenitor cell. The cell population used for this separation method can be derived, for example, from neural tissue which can include neural cells, non-neural cells, or both. Expression of Daedalos can be evaluated according to this method by using any of the techniques described herein or known in the art, e.g., mRNA or protein analysis, e.g., Western blot immunoassay, immunohistology, fluorescence activated cell sorting (FACS), radioimmunoassay (RIA), fluorescent immunoassay, enzyme linked immunosorbent assay (ELISA), or an immunoassay that uses a solid support, e.g., latex beads.

Diagnostic Methods

Another aspect of the invention relates to diagnostic methods. These methods permit a determination of, based upon expression of Daedalos in a cell of the subject, whether a subject is at risk for (or has) a neural cell related disorder. These methods involve analyzing a cell of the subject, either in vitro or in vivo, to determine the subject's risk for a neural cell related disorder, e.g., a neural cell proliferative disorder.

In one embodiment, expression of Daedalos is evaluated in a cell of the subject, e.g., a cell derived from neural tissue. A subject can be determined to be at risk for a neural cell related disorder based upon an increased expression of Daedalos in a cell of the subject as compared to the level of expression of Daedalos in the same cell type of a subject not at risk for the disorder. Expression of Daedalos can be detected by methods known in the art as described herein, e.g., detection of Daedalos mRNA or of Daedalos protein.

In another embodiment, a subject is determined to be at risk for a neural cell related disorder by detecting an abnormality in a Daedalos gene. For example, a mutation in a Daedalos gene, e.g., a missense mutation, a nonsense mutation, or a mutation in a regulatory region of the gene, can result in a defective or inactive Daedalos protein product that is associated with a neural cell related disorder, e.g., a disorder related to inappropriate proliferation and/or differentiation of neural cells. An abnormality in a Daedalos gene can be detected in a variety of ways, e.g., PCR analysis of genomic DNA or cDNA, restriction fragment length polymorphism analysis, or analysis of a Daedalos protein by gel electrophoresis.

Methods of Treatment

Another aspect of the invention relates to methods of treating disorder, e.g., a neural cell related disorder. Such methods can include modulating the expression of Daedalos in a cell of a subject in vivo or in vitro. The subject can either be at risk for or have a disorder, e.g., a neural cell related disorder. Neural cell related disorders can include disorders associated with neurodegeneration or excessive or unwanted neural cells. For example, neurodegeneration can be the result of disease, injury and/or aging. Neurodegeneration refers to an abnormality of a neural cell including, but not limited to, physical degeneration and/or death of neural cells, abnormal growth patterns of neural cells, abnormal connections between neural cells, and/or under or over production of a substance or substances, e.g., a neurotransmitter, by neural cells. Neurodegenerative disorders can include Parkinson's disease, Alzheimer's disease, ischemic damage such as stroke or spinal chord trauma, epilepsy, or multiple sclerosis. Other neural cell related disorders associated with excessive or unwanted neural cells can include proliferative disorders such as cancer, e.g., neuroma. In one example, the neural cell related disorder is characterized by insufficient neural cell differentiation. In another example, the neural cell related disorder can be characterized by unwanted or excessive neural cell differentiation.

A disorder, e.g., a neural cell related disorder, can be treated by increasing or decreasing the level of Daedalos in a cell of the subject. For example, Daedalos levels can be increased in a cell (in vitro or in vivo) to reduce neural cell differentiation. In addition, agents which promote neural cell proliferation can be used to allow expansion of neural progenitor cells prior to differentiation. Such methods can be used to treat, e.g., neurodegenerative disorders. By increasing Daedalos expression, disorders can be treated that are characterized by excessive or unwanted neural cell differentiation. In other aspects, Daedalos expression levels can be decreased to reduce or inhibit unwanted or excessive neural cell proliferation and/or insufficient neural cell differentiation. Such methods can be used, e.g., to treat neural cell proliferative disorders such as neuroma.

The level of Daedalos in a cell can be increased by a variety of methods, e.g., by administering to a cell: (1) a Daedalos polypeptide, fragment, or analog thereof; (2) a nucleic acid encoding a Daedalos polypeptide, fragment, or analog thereof; or (3) an agent that increases expression of the endogenous Daedalos gene of a cell.

Nucleic acid constructs encoding a Daedalos polypeptide can be used as a part of a gene therapy protocol to deliver nucleic acids encoding either an agonistic or antagonistic form of a Daedalos polypeptide. The invention features expression vectors for in vivo transfection and expression of a Daedalos polypeptide in particular cell types (e.g., neural cells) so as to reconstitute the function of, enhance the function of, or alternatively, antagonize the function of a Daedalos polypeptide in a cell in which the polypeptide is expressed or misexpressed.

Expression constructs of Daedalos polypeptide or Daedalos agonist or antagonists, may be administered in any biologically effective carrier, e.g. any formulation or composition capable of effectively delivering the subject gene to cells in vivo. Approaches include insertion of the subject gene into viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA encoding an Daedalos polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid, as discussed further below.

In addition to viral transfer methods, such as those described herein, non-viral methods can also be employed to cause expression of a Daedalos polypeptide or agonist or antagonist of Daedalos in the tissue of a mammal, such as a human. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes.

In a representative embodiment, the subject can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO91/06309; Japanese patent application 1047381; and European patent publication EP-A-43075).

In clinical settings, the gene delivery systems for the therapeutic Daedalos gene or gene encoding a Daedalos antagonist can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). In a preferred embodiment of the invention, the subject gene is targeted to neural cells.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

In addition, the levels of Daedalos expression in a cell can be decreased by various methods known in the art, e.g., antisense, ribozymes, antibodies, small molecule inhibitors, or compounds the suppress expression of the Daedalos gene, as described herein below.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included in the invention.

Administration

An agent which modulates the level of expression of Daedalos can be administered to a subject by standard methods. For example, the agent can be administered by any of a number of different routes including intravenous, intradermal, subcutaneous, oral (e.g., inhalation), transdermal (topical), and transmucosal. In one embodiment, the modulating agent can be administered orally. In another embodiment, the agent is administered by injection, e.g., intramuscularly, or intravenously.

The agent which modulates protein levels, e.g., nucleic acid molecules, polypeptides, fragments or analogs, modulators, and antibodies (also referred to herein as "active compounds") can be incorporated into pharmaceutical compositions suitable for administration to a subject, e.g., a human. Such compositions typically include the nucleic acid molecule, polypeptide, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a small molecule, Daedalos nucleic acid, polypeptide, or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., PNAS 91:3054–3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

Gene Therapy

The nucleic acids described herein, e.g., a nucleic acid encoding a Daedalos described herein, or an antisense nucleic acid, can be incorporated into gene constructs to be used as a part of a gene therapy protocol to deliver nucleic acids encoding either an agonistic or antagonistic form of a Daedalos described herein. The invention features expression vectors for in vivo transfection and expression of a Daedalos molecule described herein in particular cell types so as to reconstitute the function of, or alternatively, antagonize the function of the component in a cell in which that polypeptide is misexpressed. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO4 precipitation carried out in vivo.

A preferred approach for in vivo introduction of nucleic acid into a cell is by use of a viral vector containing nucleic acid, e.g. a cDNA, encoding a Daedalos described herein. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pU, pZIP, pWE and pEM which are known to those skilled in the art. Examples of suitable packaging virus lines for preparing both ecotropic and amphotropic retroviral systems include *Crip, *Cre, *2 and *Am. Retroviruses have been used to introduce a variety of genes into many different cell types, including epithelial cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) Curr. Topics in Micro. and Immunol. 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:3239; Tratschin et al. (1984) J. Virol. 51:611–619; and Flotte et al. (1993) J. Biol. Chem. 268:3781–3790).

In addition to viral transfer methods, such as those illustrated above, non-viral methods can also be employed to cause expression of Daedalos in the tissue of a subject. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al. (2001) J Invest Dermatol. 116(1):131–135; Cohen et al. (2000) Gene Ther 7(22):1896–905 Tam et al. (2000) Gene Ther 7(21):1867–74.

In a representative embodiment, a gene encoding a Daedalos can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO91/06309; Japanese patent application 1047381; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Cell Therapy

A Daedalos molecule described herein can also be increased in a subject by introducing into a cell, e.g., neural progenitor cell, neural cell, or non-neural cell, a nucleotide sequence that modulates the production of Daedalos, e.g., a nucleotide sequence encoding Daedalos, a polypeptide or functional fragment or analog thereof, a promoter sequence, e.g., a promoter sequence from a Daedalos gene or from another gene; an enhancer sequence, e.g., 5' untranslated region (UTR), e.g., a 5' UTR from a Daedalos gene or from another gene, a 3' UTR, e.g., a 3' UTR from a Daedalos gene or from another gene; a polyadenylation site; an insulator sequence; or another sequence that modulates the expression of the Daedalos molecule. The cell can then be introduced into the subject.

Primary and secondary cells to be genetically engineered can be obtained from a variety of tissues and include cell types which can be maintained propagated in culture. For example, primary and secondary cells include fibroblasts, glial cells, neural progenitor cells, neural cells, formed elements of the blood (e.g., lymphocytes, bone marrow cells), muscle cells (myoblasts) and precursors of these somatic cell types, keratinocytes, epithelial cells (e.g., mammary epithelial cells, intestinal epithelial cells), endothelial cells. Primary cells are preferably obtained from the individual to whom the genetically engineered primary or secondary cells are administered. However, primary cells may be obtained for a donor (other than the recipient).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of secondary cells which have been passaged one or more times.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding a Daedalos, or an agonist or antagonist thereof, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous sequence. An exogenous nucleic acid sequence can be introduced into a primary or secondary cell by homologous recombination as described, for example, in U.S. Pat. No. 5,641,670, the contents of which are incorporated herein by reference. The transfected primary or secondary cells may also include DNA encoding a selectable marker which confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used. The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electrophoration, all of which are routine in the art.

Transfected primary or secondary cells undergo a sufficient number of doublings to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intraplanchnic, intraperitoneal (including intraomental), intramuscularly implantation) can be used. One implanted in individual, the transfected cells produce the product encoded by the heterologous DNA or are affected by the heterologous DNA itself. For example, an individual who suffers from a neural disorder is a candidate for implantation of cells producing a Daedalos molecule described herein.

An immunosuppressive agent e.g., drug, or antibody, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) N. Engl. J. Med. 327:1549; Spencer et al. (1992) N. Engl. J. Med. 327:1541' Widner et al. (1992) n. Engl. J. Med. 327:1556). Dosage values may vary according to factors such as the disease state, age, sex, and weight of the individual.

Methods of Controlling Cell Differentiation

Another aspect of the invention relates to methods of controlling cell differentiation by modulating expression of Daedalos in a cell. The cell can be either a neural cell, e.g., a neural progenitor cell or a committed neural cell, or a non-neural cell. Modulating the expression of Daedalos in a cell can be used to control the neural differentiation of the cell.

In one embodiment, Daedalos expression in a cell is increased, e.g., by treating the cell with a compound that causes increased expression of Daedalos. This increase in Daedalos expression can inhibit or antagonize neural differentiation in a cell. This is desirable, for example, in a cell characterized by excessive neural differentiation or as part of a technique to maintain a population of neural progenitor cells by blocking their differentiation.

Daedalos expression in a cell can be increased in a variety of ways. For example, a Daedalos polypeptide, fragment, or analog thereof can be added to a cell. A peptide can either be applied directly to a cell or a cell can be treated in a manner that allows for a more efficient uptake of the peptide by the cell.

In another example, a nucleic acid encoding a Daedalos polypeptide, fragment, or analog thereof can be added to a cell. Examples of nucleic acids are the nucleic acid vectors described herein for use in gene therapy methods. The nucleic acid can include all or a part of the Daedalos coding region, 5' regulatory sequences such as a promoter (from Daedalos or another gene) and/or an enhancer (from Daedalos or another gene); and/or 3' regulatory sequences such as a 3' untranslated region, e.g., a polyadenylation site.

In another example, a cell can be treated with an agent that increases the expression of the endogenous Daedalos gene of the cell. The agent can be, e.g., a compound that binds a Daedalos promoter or that alters the regulatory sequence of the Daedalos gene.

In another embodiment, Daedalos expression in a cell is decreased, e.g., by treating the cell with a compound that causes decreased expression of Daedalos. This decrease in Daedalos expression can result in enhanced neural differentiation in a cell. This is desirable, for example, in a cell characterized by insufficient neural differentiation and/or unwanted neural cell proliferation, e.g., neuroma or as part of a technique to create a population of differentiated neural cells by encouraging the differentiation of neural progenitor cells.

Daedalos expression can be decreased in a cell in a variety of ways. In one example, a compound can be administered to a cell that causes a decrease in Daedalos expression by binding to a Daedalos nucleic acid sequence. Examples of such compounds include antisense nucleic acid and ribozymes. In another example, a compound can cause a decrease in Daedalos expression by binding to a Daedalos polypeptide. Examples of such compounds include antibodies, small molecules, and peptides. Additionally, a compound can cause decreased expression of Daedalos by reducing expression of an endogenous Daedalos gene in the cell.

In one embodiment, the invention provides methods for obtaining a population of neural progenitor cells. According to these methods, a cell sample is provided, either in vitro or in vivo, containing a neural progenitor cell and the level of Daedalos is increased in the cell sample. Increasing the level of Daedalos expressed in a neural progenitor cell can have various effects, e.g., it may prevent differentiation or cause proliferation of the neural progenitor cell. These methods can also include steps of increasing the level of other compounds in the cell sample, e.g., FGF-2 or EGF. These compounds can cause the proliferation of a neural progenitor cell while Daedalos prevents its differentiation.

Also included in the invention is a method of obtaining a population of neural cells by inhibiting the expression or activity of Daedalos in a neural progenitor cell. Inhibition of the expression or activity of Daedalos in a neural progenitor cell can result in the differentiation of the neural progenitor cell. This method therefore allows for the expansion, in vitro or in vivo, of a population of differentiated, committed neural cells. Expression or activity of Daedalos can be inhibited by treating a cell with a compound described herein. The compound can, e.g., interfere with a Daedalos mRNA, a Daedalos protein, or a Daedalos gene in a cell.

Neural cells, e.g., differentiated neural cells, expanded in vivo or in vitro by the methods described above can be used to treat, for example, neurodegenerative disorders. In one aspect, the neural cells can be expanded in vitro and then introduced into an area of neurodegeneration in a subject. The neural cells can be introduced into a subject by any route of administration which results in delivery of the cells to the desired location in the subject, e.g., direct stereotaxic injection. In another aspect, the methods described above can be used to allow proliferation of neural progenitor cells and/or differentiation in vivo at a site of neurodegeneration.

Transgenic Animals

The invention includes transgenic animals which include cells (of that animal) which contain a Daedalos transgene and which preferably (though optionally) express (or misexpress) an endogenous or exogenous Daedalos gene in one or more cells in the animal.

The Daedalos transgene can encode a mutant Daedalos polypeptide. Such animals can be used as disease models or can be used to screen for agents effective at correcting the misexpression of Daedalos. Alternatively, the Daedalos transgene can encode the wild-type forms of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns. Temporal patterns of expression can be provided by, for example, conditional recombination systems or prokaryotic transcriptional regulatory sequences. In preferred embodiments, the transgenic animal carries a "knockout" Daedalos gene, i.e., a deletion of all or a part of the Daedalos gene.

Genetic techniques which allow for the expression of transgenes, that are regulated in vivo via site-specific genetic manipulation, are known to those skilled in the art. For example, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject Daedalos gene. For example, excision of a target sequence which interferes with the expression of a recombinant Daedalos gene, such as one which encodes an agonistic homolog, can be designed to activate expression of that gene. This interference with expression of the protein can result from a variety of mechanisms, such as spatial separation of the Daedalos gene from the promoter element or an internal stop codon.

Moreover, the transgene can be made so that the coding sequence of the gene is flanked with recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation. See e.g., descriptions of the crelloxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694). Genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the recombinant Daedalos gene can be regulated via control of recombinase expression.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the Daedalos transgene could remain silent into adulthood until "turned on" by the introduction of the trans-activator.

Also included is a transgenic animal, or a cell or tissue therefrom, having a transgene including a Daedalos control region operably linked to a nucleic acid encoding a detectable marker, e.g., a fluorescent or luminescent marker, e.g., GFP. The detectable marker thus acts as a surrogate for evaluating Daedalos expression in the transgenic animal. For example, if the detectable marker is a fluorescent marker, e.g., GFP, expression of the marker can be detected by confocal microscopy of a tissue, e.g., skin or nerve tissue, of the animal.

Production of Fragments and Analogs

The invention provides the primary amino acid structure of a Daedalos polypeptide. Once an example of this core structure has been provided, one skilled in the art can alter the disclosed structure by producing fragments or analogs, and testing the newly produced structures for activity. Examples of prior art methods which allow the production and testing of fragments and analogs are discussed below. These, or analogous methods can be used to make and screen fragments and analogs of a Daedalos polypeptide having at least one biological activity e.g., which react with an antibody (e.g., a monoclonal antibody) specific for a Daedalos polypeptide.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Production of Altered DNA and Peptide Sequences: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complementary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Production of Altered DNA and Peptide Sequences: Methods for Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765[1978]).

Cassette Mutagenesis

Another method for preparing variants, cassette mutagenesis, is based on the technique described by Wells et al. (*Gene*, 34:315 [1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants, e.g., a library of variants which is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to an antibody specific for a Daedalos polypeptide. Each of the techniques described below is amenable to high through-put analysis for screening large numbers of sequences created, e.g., by random mutagenesis techniques.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988)

*Bio/Tech.* 6, 1080–1083). Surface proteins of other bacterial species have also served as peptide fusion partners. Examples include the Staphylococcus protein A and the outer membrane protease IgA of Neisseria (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) PNAS USA 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of a protein of interest is identified, such as the primary amino acid sequence of Daedalos polypeptide as disclosed herein, it is routine to perform for one skilled in the art to obtain analogs and fragments.

Peptide Analogs of Daedalos

Peptide analogs of a Daedalos polypeptide are preferably less than 400, 300, 200, 150, 130, 110, 90, 70 amino acids in length, preferably less than 50 amino acids in length, most preferably less than 30, 20 or 10 amino acids in length. In preferred embodiments, the peptide analogs of a Daedalos polypeptide are at least about 10, 20, 30, 50, 100 or 130 amino acids in length.

Peptide analogs of a Daedalos polypeptide have preferably at least about 60%, 70%, 80%, 85%, 90%, 95% or 99% homology or sequence similarity with the naturally occurring Daedalos polypeptide.

Peptide analogs of a Daedalos polypeptide differ from the naturally occurring Daedalos polypeptide by at least (but not more than) 1, 2, 5, 10 or 20 amino acid residues; preferably, however, they differ in less than 15, 10 or 5 amino acid residues from the naturally occurring Daedalos polypeptide.

Useful analogs of a Daedalos polypeptide can be agonists or antagonists. Antagonists of a Daedalos polypeptide can be molecules which form dimers with a member of the Ikaros family but which lack some additional biological activity such as transcriptional activation of genes that control neural development. Daedalos antagonists and agonists are derivatives which can modulate, e.g., inhibit or promote, neural maturation and function.

Antisense Nucleic Acid Sequences

Nucleic acid molecules which are antisense to a nucleotide encoding a Daedalos molecule described herein can be used as an agent which inhibits expression of Daedalos. An "antisense" nucleic acid includes a nucleotide sequence which is complementary to a "sense" nucleic acid encoding the component, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire coding strand, or to only a portion thereof. For example, an antisense nucleic acid molecule which antisense to the "coding region" of the coding strand of a nucleotide sequence encoding the component can be used.

The coding strand sequences encoding Daedalos are known. Given the coding strand sequences encoding these proteins, antisense nucleic acids can be designed according to the rules of Watson and Crick base pairing. The antisense nucleic acid molecule can be complementary to the entire coding region of mRNA, but more preferably is an oligonucleotide which is antisense to only a portion of the coding or noncoding region of mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

Antibodies

The invention also includes antibodies specifically reactive with a subject Daedalos polypeptide. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject Daedalos polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the Daedalos polypeptide of the invention.

The term "antibody", as used herein, intended to include fragments thereof which are also specifically reactive with a Daedalos polypeptide. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Both monoclonal and polyclonal antibodies (Ab) directed against Daedalos polypeptides, or fragments or analogs thereof, and antibody fragments such as Fab' and F(ab')$_2$, can be used to block the action of a Daedalos polypeptide and allow the study of the role of a Daedalos polypeptide of the present invention.

Antibodies which specifically bind Daedalos polypeptide epitopes can also be used in immunohistochemical staining of tissue samples in order to evaluate the abundance and pattern of expression of Daedalos polypeptide. Anti-Daedalos polypeptide antibodies can be used diagnostically in immuno-precipitation and immuno-blotting to detect and evaluate wild type or mutant Daedalos polypeptide levels in tissue or bodily fluid as part of a clinical testing procedure. Likewise, the ability to monitor Daedalos polypeptide levels in an individual can allow determination of the efficacy of a given treatment regimen for an individual afflicted with disorders associated with modulation of lymphocyte differentiation and/or proliferation. The level of a Daedalos polypeptide can be measured in tissue, such as produced by biopsy.

Another application of anti-Daedalos antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject Daedalos polypeptide can then be detected with antibodies, as, for example, reacting nitrocellulose filters lifted from infected plates with anti-Daedalos polypeptide antibodies. Phage, scored by this assay, can then be isolated from the infected plate. Thus, the presence of Daedalos homologs can be detected and cloned from other animals, and alternate isoforms (including splicing variants) can be detected and cloned from human sources.

Drug Screening Assays

By making available purified and recombinant-Daedalos polypeptides, the present invention provides assays which can be used to screen for drugs which are either agonists or antagonists of the normal cellular function, in this case, of the subject Daedalos polypeptide. In one embodiment, the assay evaluates the ability of a compound to modulate binding between a Daedalos polypeptide and a naturally occurring ligand, e.g., an antibody specific for a Daedalos polypeptide. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target.

All publications and patents cited in this application are hereby incorporated by reference in their entirety.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed:

1. A method of identifying a neural progenitor cell, comprising:
   providing a sample of cells or tissue; and
   evaluating the level of expression of Daedalos in a cell of the sample,
   wherein if the cell has a higher level of expression of Daedalos as compared to a control, it is identified as a neural progenitor cell.

2. The method of claim 1, wherein evaluating the level of expression of Daedalos comprises detecting Daedalos mRNA.

3. The method of claim 1, wherein evaluating the level of expression of Daedalos comprises detecting Daedalos protein.

4. The method of claim 1, wherein the sample of cells or tissue contains neural progenitor cells and non-neural progenitor cells.

5. The method of claim 1, wherein the sample is neural cells or tissue.

6. A method of identifying the stage of neurogenesis of a cell, comprising:
   evaluating the level of expression of Daedalos in the cell,
   wherein if the cell has a higher level of expression of Daedalos as compared to a control, it is identified as a neural progenitor cell and if the cell has a lower level of expression of Daedalos as compared to a control, it is identified as a differentiated cell.

7. The method of claim 6, further comprising the step of isolating a first cell, based upon its stage of neurogenesis, from a second cell characterized by a different stage of neurogenesis.

8. The method of claim 6, wherein evaluating the level of expression of Daedalos comprises detecting Daedalos mRNA.

9. The method of claim 6, wherein evaluating the level of expression of Daedalos comprises detecting Daedalos protein.

* * * * *

SEQUENCE LISTING

<160> NUMBER OF SEQ ID NOS: 13

<210> SEQ ID NO 1
<211> LENGTH: 537
<212> TYPE: PRT
<213> ORGANISM: Mus musculus

<400> SEQUENCE: 1

```
Met Glu Ser Leu Phe Cys Glu Ser Ser Gly Asp Ser Ser Leu Glu Lys
 1               5                  10                  15

Glu Phe Leu Gly Ala Pro Val Gly Pro Ser Val Ser Thr Pro Asn Ser
            20                  25                  30

Gln His Ser Ser Pro Ser Arg Ser Leu Ser Ala Asn Ser Ile Lys Val
        35                  40                  45

Glu Met Tyr Ser Asp Glu Glu Ser Ser Arg Leu Leu Gly Pro Asp Glu
    50                  55                  60

Arg Leu Leu Asp Lys Asp Asp Ser Val Ile Val Glu Asp Ser Leu Ser
65                  70                  75                  80

Glu Pro Leu Gly Tyr Cys Asp Gly Ser Gly Pro Glu Pro His Ser Pro
                85                  90                  95

Gly Gly Ile Arg Leu Pro Asn Gly Lys Leu Lys Cys Asp Val Cys Gly
            100                 105                 110

Met Val Cys Ile Gly Pro Asn Val Leu Met Val His Lys Arg Ser His
        115                 120                 125

Thr Gly Glu Arg Pro Phe His Cys Asn Gln Cys Gly Ala Ser Phe Thr
    130                 135                 140

Gln Lys Gly Asn Leu Leu Arg His Ile Lys Leu His Ser Gly Glu Lys
145                 150                 155                 160

Pro Phe Lys Cys Pro Phe Cys Asn Tyr Ala Cys Arg Arg Arg Asp Ala
                165                 170                 175
```

```
Leu Thr Gly His Leu Arg Thr His Ser Val Ser Ser Pro Thr Val Gly
            180                 185                 190

Lys Pro Tyr Lys Cys Asn Tyr Cys Gly Arg Ser Tyr Lys Gln Gln Ser
        195                 200                 205

Thr Leu Glu Glu His Lys Glu Arg Cys His Asn Tyr Leu Gln Ser Leu
    210                 215                 220

Ser Thr Asp Ala Gln Ala Leu Thr Gly Gln Pro Gly Asp Glu Ile Arg
225                 230                 235                 240

Asp Leu Glu Met Val Pro Asp Ser Met Leu His Pro Ser Thr Glu Arg
                245                 250                 255

Pro Thr Phe Ile Asp Arg Leu Ala Asn Ser Leu Thr Lys Arg Lys Arg
            260                 265                 270

Ser Thr Pro Gln Lys Phe Val Gly Glu Lys Gln Met Arg Phe Ser Leu
        275                 280                 285

Ser Asp Leu Pro Tyr Asp Val Asn Ala Ser Gly Gly Tyr Glu Lys Asp
    290                 295                 300

Val Glu Leu Val Ala His His Gly Leu Glu Pro Gly Phe Gly Gly Ser
305                 310                 315                 320

Leu Ala Phe Val Gly Thr Glu His Leu Arg Pro Leu Arg Leu Pro Pro
                325                 330                 335

Thr Asn Cys Ile Ser Glu Leu Thr Pro Val Ile Ser Ser Val Tyr Thr
            340                 345                 350

Gln Met Gln Pro Ile Pro Ser Arg Leu Glu Leu Pro Gly Ser Arg Glu
        355                 360                 365

Ala Gly Glu Gly Pro Glu Asp Leu Gly Asp Gly Pro Leu Leu Tyr
    370                 375                 380

Arg Ala Arg Gly Ser Leu Thr Asp Pro Gly Ala Ser Pro Ser Asn Gly
385                 390                 395                 400

Cys Gln Asp Ser Thr Asp Thr Glu Ser Asn His Glu Asp Arg Ile Gly
                405                 410                 415

Gly Val Val Ser Leu Pro Gln Gly Pro Pro Gln Pro Pro Pro Thr
            420                 425                 430

Ile Val Val Gly Arg His Ser Pro Ala Tyr Ala Lys Glu Asp Pro Lys
        435                 440                 445

Pro Gln Glu Gly Leu Leu Arg Gly Thr Pro Gly Pro Ser Lys Glu Val
    450                 455                 460

Leu Arg Val Val Gly Glu Ser Gly Glu Pro Val Lys Ala Phe Lys Cys
465                 470                 475                 480

Glu His Cys Arg Ile Leu Phe Leu Asp His Val Met Phe Thr Ile His
                485                 490                 495

Met Gly Cys His Gly Phe Arg Asp Pro Phe Glu Cys Asn Ile Cys Gly
            500                 505                 510

Tyr His Ser Gln Asp Arg Tyr Glu Phe Ser Ser His Ile Val Arg Gly
        515                 520                 525

Glu His Lys Val Gly Ser Cys Arg Ile
    530                 535

<210> SEQ ID NO 2
<211> LENGTH: 532
<212> TYPE: PRT
<213> ORGANISM: Mus musculus

<400> SEQUENCE: 2

Met His Cys Thr Leu Thr Met Glu Thr Asp Ala Ile Asp Gly Tyr Ile
1               5                   10                  15
```

-continued

```
Thr Cys Asp Asn Glu Leu Ser Pro Glu Gly Glu His Ala Asn Met Ala
                20                  25                  30
Ile Asp Leu Thr Ser Ser Thr Pro Asn Gly Gln Gln Ala Ser Pro Ser
             35                  40                  45
His Met Thr Ser Thr Asn Ser Val Lys Leu Glu Met Gln Ser Asp Glu
         50                  55                  60
Glu Cys Asp Arg Gln Pro Leu Ser Arg Glu Asp Glu Ile Arg Gly His
 65                  70                  75                  80
Asp Glu Gly Ser Ser Leu Glu Glu Ala Leu Ile Glu Ser Ser Glu Val
                 85                  90                  95
Ala Asp Asn Arg Lys Val Gln Asp Leu Gln Gly Glu Arg Gly Ile Arg
            100                 105                 110
Leu Pro Asn Gly Lys Leu Lys Cys Asp Val Cys Gly Met Val Cys Ile
        115                 120                 125
Gly Pro Asn Val Leu Met Val His Lys Arg Ser His Thr Gly Glu Arg
    130                 135                 140
Pro Phe His Cys Asn Gln Cys Gly Arg Ser Phe Thr Gln Lys Gly Asn
145                 150                 155                 160
Leu Leu Arg His Ile Lys Leu His Ser Gly Glu Lys Pro Phe Lys Cys
                165                 170                 175
Pro Phe Cys Ser Tyr Ala Cys Arg Arg Arg Asp Ala Leu Thr Gly His
            180                 185                 190
Leu Arg Thr His Ser Val Gly Lys Pro His Lys Cys Asn Tyr Cys Gly
        195                 200                 205
Arg Ser Tyr Lys Gln Arg Thr Ser Leu Glu Glu His Lys Glu Arg Cys
    210                 215                 220
His Asn Tyr Leu Gln Asn Val Ser Met Glu Ala Ala Gly Gln Val Met
225                 230                 235                 240
Ser His His Val Pro Pro Met Glu Asp Cys Lys Glu Gln Glu Pro Ile
                245                 250                 255
Met Asp Asn Asn Ile Ser Leu Val Ala Phe Glu Arg Pro Ala Val Ile
            260                 265                 270
Glu Lys Leu Thr Ala Asn Met Gly Lys Arg Lys Ser Ser Thr Pro Gln
        275                 280                 285
Lys Phe Val Gly Glu Lys Leu Met Arg Phe Ser Tyr Pro Asp Ile His
    290                 295                 300
Phe His Met Asn Leu Thr Tyr Glu Lys Glu Ala Glu Leu Met Gln Ser
305                 310                 315                 320
His Met Met Asp Gln Ala Ile Asn Asn Ala Ile Thr Tyr Leu Gly Ala
                325                 330                 335
Glu Ala Leu His Pro Leu Met Gln His Ala Pro Ser Thr Ile Ala Glu
            340                 345                 350
Val Ala Pro Val Ile Ser Ser Ala Tyr Ser Gln Val Tyr His Pro Asn
        355                 360                 365
Arg Ile Glu Arg Pro Ile Ser Arg Glu Thr Ser Asp Ser His Glu Asn
    370                 375                 380
Asn Met Asp Gly Pro Ile Ser Leu Ile Arg Pro Lys Ser Arg Pro Gln
385                 390                 395                 400
Glu Arg Glu Ala Ser Pro Ser Asn Ser Cys Leu Asp Ser Thr Asp Ser
                405                 410                 415
Glu Ser Ser His Asp Asp Arg Gln Ser Tyr Gln Gly Asn Pro Ala Leu
            420                 425                 430
```

```
Asn Pro Lys Arg Lys Gln Ser Pro Ala Tyr Met Lys Glu Asp Val Lys
        435                 440                 445

Ala Leu Asp Ala Thr Lys Ala Pro Lys Gly Ser Leu Lys Asp Ile Tyr
    450                 455                 460

Lys Val Phe Asn Gly Glu Gly Glu Gln Ile Arg Ala Phe Lys Cys Glu
465                 470                 475                 480

His Cys Arg Val Leu Phe Leu Asp His Val Met Tyr Thr Ile His Met
                485                 490                 495

Gly Cys His Gly Tyr Arg Asp Pro Leu Glu Cys Asn Ile Cys Gly Tyr
            500                 505                 510

Arg Ser Gln Asp Arg Tyr Glu Phe Ser Ser His Ile Val Gly Gly Gln
        515                 520                 525

His Thr Phe His
    530

<210> SEQ ID NO 3
<211> LENGTH: 507
<212> TYPE: PRT
<213> ORGANISM: Mus musculus

<400> SEQUENCE: 3

Met Glu Asp Ile Gln Pro Thr Val Glu Leu Lys Ser Thr Glu Glu Gln
1               5                   10                  15

Pro Leu Pro Thr Glu Ser Pro Asp Ala Leu Asn Asp Tyr Ser Leu Pro
            20                  25                  30

Lys Pro His Glu Ile Glu Asn Val Asp Ser Arg Glu Ala Pro Ala Asn
        35                  40                  45

Glu Asp Glu Asp Ala Gly Glu Asp Ser Met Lys Val Lys Asp Glu Tyr
50                  55                  60

Ser Asp Arg Asp Glu Asn Ile Met Lys Pro Glu Pro Met Gly Asp Ala
65                  70                  75                  80

Glu Glu Ser Glu Met Pro Tyr Ser Tyr Ala Arg Glu Tyr Ser Asp Tyr
                85                  90                  95

Glu Ser Ile Lys Leu Glu Arg His Val Pro Tyr Asp Asn Ser Arg Pro
            100                 105                 110

Thr Ser Gly Lys Met Met Cys Asp Val Cys Gly Leu Ser Cys Ile Ser
        115                 120                 125

Phe Asn Val Leu Met Val His Lys Arg Ser His Thr Gly Glu Arg Pro
130                 135                 140

Phe Gln Cys Asn Gln Cys Gly Ala Ser Phe Thr Gln Lys Gly Asn Leu
145                 150                 155                 160

Leu Arg His Ile Lys Leu His Thr Gly Glu Lys Pro Phe Lys Cys His
                165                 170                 175

Leu Cys Asn Tyr Ala Cys Gln Arg Arg Asp Ala Leu Thr Gly His Leu
            180                 185                 190

Arg Thr His Ser Val Glu Lys Pro Tyr Lys Cys Glu Phe Cys Gly Arg
        195                 200                 205

Ser Tyr Lys Gln Arg Ser Ser Leu Glu Glu His Lys Glu Arg Cys Arg
    210                 215                 220

Ala Phe Leu Gln Asn Pro Asp Leu Gly Asp Ala Ala Ser Val Glu Ala
225                 230                 235                 240

Arg His Ile Lys Ala Glu Met Gly Ser Glu Arg Ala Leu Val Leu Asp
                245                 250                 255

Arg Leu Ala Ser Asn Val Ala Lys Arg Lys Ser Ser Met Pro Gln Lys
            260                 265                 270
```

```
Phe Ile Gly Glu Lys Arg His Cys Phe Asp Ala Asn Tyr Asn Pro Gly
            275                 280                 285

Tyr Met Tyr Glu Lys Glu Asn Glu Met Met Gln Thr Arg Met Met Asp
        290                 295                 300

Gln Ala Ile Asn Asn Ala Ile Ser Tyr Leu Gly Ala Glu Ala Phe Arg
305                 310                 315                 320

Pro Leu Val Gln Thr Pro Pro Ala Pro Thr Ser Glu Met Val Pro Val
                325                 330                 335

Ile Ser Ser Val Tyr Pro Ile Ala Leu Thr Arg Ala Asp Met Pro Met
            340                 345                 350

Gly Ala Pro Gln Glu Met Glu Lys Lys Arg Ile Leu Leu Pro Glu Lys
        355                 360                 365

Ile Leu Pro Ser Glu Arg Gly Leu Ser Pro Asn Asn Ser Ala Gln Asp
    370                 375                 380

Ser Thr Asp Thr Asp Ser Asn His Glu Asp Arg Gln His Leu Tyr Gln
385                 390                 395                 400

Gln Ser His Val Val Leu Pro Gln Ala Arg Asn Gly Met Pro Leu Leu
                405                 410                 415

Lys Glu Val Pro Arg Ser Phe Glu Leu Leu Lys Pro Pro Pro Ile Cys
            420                 425                 430

Leu Arg Asp Ser Ile Lys Val Ile Asn Lys Glu Gly Glu Val Met Asp
        435                 440                 445

Val Phe Arg Cys Asp His Cys His Val Leu Phe Leu Asp Tyr Val Met
    450                 455                 460

Phe Thr Ile His Met Gly Cys His Gly Phe Arg Asp Pro Phe Glu Cys
465                 470                 475                 480

Asn Met Cys Gly Tyr Arg Ser His Asp Arg Tyr Glu Phe Ser Ser His
                485                 490                 495

Ile Ala Arg Gly Glu His Arg Ala Met Leu Lys
            500                 505

<210> SEQ ID NO 4
<211> LENGTH: 515
<212> TYPE: PRT
<213> ORGANISM: Mus musculus

<400> SEQUENCE: 4

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
                20                  25                  30

Val Pro Glu Asp Leu Ser Thr Thr Ser Gly Ala Gln Gln Asn Ser Lys
            35                  40                  45

Ser Asp Arg Gly Met Ala Ser Asn Val Lys Val Glu Thr Gln Ser Asp
        50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Val Cys Ile Gly
        115                 120                 125

Pro Asn Val Leu Met Val His Lys Arg Ser His Thr Gly Glu Arg Pro
```

-continued

```
        130             135             140
Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Asp Ala Leu Thr Gly His Leu
                180                 185                 190

Arg Thr His Ser Val Gly Lys Pro His Lys Cys Gly Tyr Cys Gly Arg
                195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Val Cys Pro Val Ile Lys
225                 230                 235                 240

Glu Glu Thr Asn His Asn Glu Met Ala Glu Asp Leu Cys Lys Ile Gly
                245                 250                 255

Ala Glu Arg Ser Leu Val Leu Asp Arg Leu Ala Ser Asn Val Ala Lys
                260                 265                 270

Arg Lys Ser Ser Met Pro Gln Lys Phe Leu Gly Asp Lys Cys Leu Ser
    275                 280                 285

Asp Met Pro Tyr Asp Ser Ala Asn Tyr Glu Lys Glu Asp Met Met Thr
    290                 295                 300

Ser His Val Met Asp Gln Ala Ile Asn Asn Ala Ile Asn Tyr Leu Gly
305                 310                 315                 320

Ala Glu Ser Leu Arg Pro Leu Val Gln Thr Pro Pro Gly Ser Ser Glu
                325                 330                 335

Val Val Pro Val Ile Ser Ser Met Tyr Gln Leu His Lys Pro Pro Ser
                340                 345                 350

Asp Gly Pro Pro Arg Ser Asn His Ser Ala Gln Asp Ala Val Asp Asn
                355                 360                 365

Leu Leu Leu Leu Ser Lys Ala Lys Ser Val Ser Ser Glu Arg Glu Ala
                370                 375                 380

Ser Pro Ser Asn Ser Cys Gln Asp Ser Thr Asp Thr Glu Ser Asn Ala
385                 390                 395                 400

Glu Glu Gln Arg Ser Gly Leu Ile Tyr Leu Thr Asn His Ile Asn Pro
                405                 410                 415

His Ala Arg Asn Gly Leu Ala Leu Lys Glu Glu Gln Arg Ala Tyr Glu
                420                 425                 430

Val Leu Arg Ala Ala Ser Glu Asn Ser Gln Asp Ala Phe Arg Val Val
                435                 440                 445

Ser Thr Ser Gly Glu Gln Leu Lys Val Tyr Lys Cys Glu His Cys Arg
450                 455                 460

Val Leu Phe Leu Asp His Val Met Tyr Thr Ile His Met Gly Cys His
465                 470                 475                 480

Gly Phe Arg Asp Pro Phe Glu Cys Asn Met Cys Gly Tyr His Ser Gln
                485                 490                 495

Asp Arg Tyr Glu Phe Ser Ser His Ile Thr Arg Gly Glu His Arg Tyr
                500                 505                 510

His Leu Ser
        515

<210> SEQ ID NO 5
<211> LENGTH: 498
<212> TYPE: PRT
<213> ORGANISM: Mus musculus
```

<400> SEQUENCE: 5

```
Met Ser Gly Ser Thr Phe Pro Thr Val Val Gly His Lys Leu Glu Ser
  1               5                  10                  15
Ile Phe Tyr Ser Ser Thr Val Ala Ala Leu Asp Arg Pro Lys Ala Gly
             20                  25                  30
Asp Ser Ser Leu Glu Lys Asp Phe Ser Asp Ala Leu Ile Gly Pro Thr
         35                  40                  45
Val Ser Thr Pro Asn Ser Arg His Ser Ser Pro Ser Arg Ser Arg Ser
 50                  55                  60
Ala Asn Ser Ile Lys Val Glu Met Tyr Gly Asp Asp Glu Ser Gly Arg
 65                  70                  75                  80
Leu Leu Ser His Glu Asp Arg Leu Ser Glu Lys Glu Asp Glu Ile Met
                 85                  90                  95
Gly Asp Asp Ser Leu Val Glu Pro Leu Gly Tyr Cys Asp Gly Pro Gly
            100                 105                 110
Gln Asp Pro His Ser Pro Gly Ile Leu Leu Pro Asn Gly Lys Leu Lys
        115                 120                 125
Cys Asp Ile Cys Gly Met Val Cys Ile Gly Pro Asn Val Leu Met Val
130                 135                 140
His Lys Arg Ser His Thr Gly Glu Arg Pro Phe His Cys Asn Gln Cys
145                 150                 155                 160
Gly Ala Pro Phe Thr Gln Lys Gly Asn Leu Leu Arg His Ile Lys Leu
                165                 170                 175
His Ser Gly Glu Lys Pro Phe Lys Cys Pro Phe Cys Asn Tyr Ala Cys
            180                 185                 190
Arg Arg Arg Asp Ala Leu Ser Gly His Leu Arg Thr His Ala Val Gly
        195                 200                 205
Lys Pro Tyr Lys Cys Asn Tyr Cys Gly Arg Ser Tyr Lys Gln Gln Asn
    210                 215                 220
Thr Leu Glu Glu His Lys Glu Arg Cys His Asn Tyr Leu Gln Ser Leu
225                 230                 235                 240
Ser Asn Glu Ala Gln His Leu Pro Ala His Pro Gly Glu Trp Gly Pro
                245                 250                 255
Gln Gly Gly Asn Cys Ile Cys Thr Arg Glu Lys Gln Met Arg Leu Ser
            260                 265                 270
Leu Ala Asp Leu Pro Tyr Glu Met Asn Ser Ser Phe Glu Lys Asp Val
        275                 280                 285
Glu Ile Val Ser His His Pro Leu Asp Thr Ala Tyr Gly Asn Ser Leu
    290                 295                 300
Ala Phe Val Gly Gly Pro Met Arg Leu Pro Pro Thr Asn Cys Ile Ser
305                 310                 315                 320
Glu Ile Thr Pro Val Ile Ser Ser Val Tyr Thr Gln Leu Gln Pro Met
                325                 330                 335
Gln Gly Arg Pro Asp Met Pro Gly Asn Arg Glu Ala Ala Glu Gly His
            340                 345                 350
Glu Asp Ile Pro Asp Gly Thr Gln Ile His Tyr Arg Gly Arg Ser Glu
        355                 360                 365
His Gly Ala Ser Pro Thr Asn Gly Cys Gln Asp Ser Asn Thr Asp Thr
    370                 375                 380
Glu Ser Asn His Glu Glu Arg Gly Ser Gln Ala Thr Ser Ser Arg Gln
385                 390                 395                 400
Ser Ser Ala Tyr Ala Lys Glu Asp Gln Arg Pro Ser Asp Gly Gly Leu
```

-continued

```
                405                 410                 415
Leu Leu Pro Ser Arg Ser Met Pro Gly Thr Ala Lys Glu Ser Leu Arg
            420                 425                 430

Val Leu Gly Glu Asp Gly Val Gln Val Lys Val Phe Lys Cys Glu His
        435                 440                 445

Cys Arg Val Leu Phe Leu Asp His Val Met Phe Thr Ile His Met Gly
    450                 455                 460

Cys His Gly Glu Arg Asp Pro Phe Glu Cys Asn Ile Cys Gly Tyr His
465                 470                 475                 480

Cys Gln Asp Arg Tyr Glu Phe Ser Ser His Ile Val Arg Gly Glu His
                485                 490                 495

Lys Val

<210> SEQ ID NO 6
<211> LENGTH: 26
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 15, 18, 21
<223> OTHER INFORMATION: n = inosine

<400> SEQUENCE: 6
tgyaaycart gyggngcnwc nttyac                                    26

<210> SEQ ID NO 7
<211> LENGTH: 26
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 6, 15, 18
<223> OTHER INFORMATION: n = inosine

<400> SEQUENCE: 7
tgrcanccca trtgnatngt rwacat                                    26

<210> SEQ ID NO 8
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 8
agggacaaca tccagggcat cacc                                      24

<210> SEQ ID NO 9
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 9
atccatggcg gtaacggtct tcct                                      24

<210> SEQ ID NO 10
<211> LENGTH: 24
<212> TYPE: DNA
```

```
<213> ORGANISM: Artificial Sequence
<220> FEATURE:
<223> OTHER INFORMATION: Synthetically generated primer

<400> SEQUENCE: 10
attctgtaac tacgcttgtc gtcg                                              24

<210> SEQ ID NO 11
<211> LENGTH: 24
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 7
<223> OTHER INFORMATION: n = inosine

<400> SEQUENCE: 11
aacaatngcc ataagcagtg tcca                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 12
catattggta caggactcct atcc                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 13
cttgaccctt atgggaagca ggaa                                              24
```